US007026288B2

(12) United States Patent
Judice et al.

(10) Patent No.: US 7,026,288 B2
(45) Date of Patent: Apr. 11, 2006

(54) PHARMACEUTICAL COMPOSITIONS CONTAINING A GLYCOPEPTIDE ANTIBIOTIC AND A CYCLODEXTRIN

(75) Inventors: J. Kevin Judice, El Granada, CA (US); Jeng Pyng Shaw, Saratoga, CA (US); YongQi Mu, Los Altos, CA (US); Michael W. Conner, Half Moon Bay, CA (US); John L. Pace, San Anselmo, CA (US)

(73) Assignee: Theravance, Inc., South San Francisco, CA (US)

( * ) Notice: Subject to any disclaimer, the term of this patent is extended or adjusted under 35 U.S.C. 154(b) by 21 days.

(21) Appl. No.: 10/930,585

(22) Filed: Aug. 31, 2004

(65) Prior Publication Data
US 2005/0026820 A1 Feb. 3, 2005

Related U.S. Application Data

(63) Continuation of application No. 09/846,893, filed on May 1, 2001, now Pat. No. 6,858,584.

(60) Provisional application No. 60/226,727, filed on Aug. 18, 2000, provisional application No. 60/213,415, filed on Jun. 22, 2000, provisional application No. 60/213,410, filed on Jun. 22, 2000, provisional application No. 60/213,417, filed on Jun. 22, 2000, provisional application No. 60/213,146, filed on Jun. 22, 2000, provisional application No. 60/213,428, filed on Jun. 22, 2000, provisional application No. 60/201,178, filed on May 2, 2000.

(51) Int. Cl.
*A61K 31/715* (2006.01)
*C07K 14/00* (2006.01)

(52) U.S. Cl. ............. 514/8; 514/2; 514/58; 424/70.13; 424/94.6; 424/278.1; 530/300; 530/402; 530/407

(58) Field of Classification Search ............. 514/8, 514/2, 58; 424/70.13, 94.6, 278.1; 530/402, 530/300, 407
See application file for complete search history.

(56) References Cited

U.S. PATENT DOCUMENTS

| 4,639,433 | A | 1/1987 | Hunt et al. |
|---|---|---|---|
| 4,643,987 | A | 2/1987 | Nagarajan et al. |
| 4,698,327 | A | 10/1987 | Nagarajan et al. |
| 4,727,064 | A | 2/1988 | Pitha |
| 4,983,586 | A | 1/1991 | Bodor |
| 5,024,998 | A | 6/1991 | Bodor |
| 5,134,127 | A | 7/1992 | Stella et al. |
| 5,324,718 | A | 6/1994 | Loftsson |
| 5,376,645 | A | 12/1994 | Stella et al. |
| 5,472,954 | A | 12/1995 | Loftsson |
| 5,591,714 | A | 1/1997 | Nagarajan et al. |
| 5,602,112 | A | 2/1997 | Rubinfeld |
| 5,624,914 | A | 4/1997 | Patel et al. |
| 5,750,509 | A | 5/1998 | Malabarba et al. |
| 5,776,912 | A | 7/1998 | Patel et al. |
| 5,804,568 | A | 9/1998 | Rubinfeld |
| 5,840,684 | A | 11/1998 | Cooper et al. |
| 5,874,418 | A | 2/1999 | Stella et al. |
| 5,916,873 | A | 6/1999 | Cooper et al. |
| 5,985,310 | A | 11/1999 | Castillo et al. |
| 6,046,177 | A | 4/2000 | Stella et al. |
| 6,048,845 | A | 4/2000 | Rubinfeld |
| 6,620,781 | B1 | 9/2003 | Linsell et al. |
| 6,635,618 | B1 | 10/2003 | Leadbetter et al. |
| 6,770,621 | B1 | 8/2004 | Linsell et al. |
| 6,828,299 | B1 | 12/2004 | Yang et al. |
| 2002/0077280 | A1 | 6/2002 | Judice et al. |
| 2003/0078371 | A1 | 4/2003 | Mu |
| 2003/0207797 | A1 | 11/2003 | Leadbetter et al. |
| 2004/0063916 | A1 | 4/2004 | Leadbetter et al. |
| 2004/0087494 | A1 | 5/2004 | Linsell et al. |
| 2004/0229775 | A1 | 11/2004 | Linsell et al. |

FOREIGN PATENT DOCUMENTS

| CA | 1 222 697 | 6/1987 |
|---|---|---|
| EP | 0 094 157 A1 | 11/1983 |
| EP | 0 335 545 B2 | 10/1989 |
| EP | 0 463 653 A1 | 1/1992 |
| EP | 0 667 353 A1 | 8/1995 |
| EP | 0 149 197 B2 | 1/1997 |
| EP | 0 816 378 A1 | 1/1998 |
| WO | 82/00251 A1 | 2/1982 |
| WO | 94/12217 A1 | 6/1994 |
| WO | 94/20136 A1 | 9/1994 |
| WO | 95/06485 A1 | 3/1995 |
| WO | WO 98/55148 A1 | 12/1998 |
| WO | WO 00/39156 A1 | 7/2000 |
| WO | WO 00/54751 A1 | 9/2000 |
| WO | WO 00/59528 A1 | 10/2000 |
| WO | WO 01/83520 A2 | 11/2001 |
| WO | WO 01/97851 A2 | 12/2001 |
| WO | WO 01/98326 A2 | 12/2001 |
| WO | WO 01/98327 A2 | 12/2001 |

(Continued)

OTHER PUBLICATIONS

U.S. Appl. No. 10/931,122, Judice et al.

(Continued)

*Primary Examiner*—Robert A. Wax
*Assistant Examiner*—Samuel W. Liu
(74) *Attorney, Agent, or Firm*—Jeffrey A. Hagenah

(57) ABSTRACT

Disclosed are pharmaceutical compositions containing a cyclodextrin and a therapeutically effective amount of a glycopeptide antibiotic or a salt thereof. Also disclosed are methods of treating a bacterial disease in a mammal by administering such pharmaceutical compositions.

8 Claims, No Drawings

FOREIGN PATENT DOCUMENTS

WO     WO 01/98328 A2     12/2001
WO     WO 01/98329 A1     12/2001

OTHER PUBLICATIONS

Allen et al., "The Role of Hydrophobic Side Chains as Determinants of Antibacterial Activity of Semisynthetic Glycopeptide Antibiotics", The Journal of Antibiotics, vol. 50, No. 8, pp 677-684 (1997).

Ge et al., "Vancomycin Derivatives That Inhibit Peptidoglycan Biosynthesis Without Binding D-Ala-D-Ala", SCIENCE, vol. 284, pp 507-511 (1999).

Nagarajan et al., "Synthesis and Antibacterial Evaluation of N-Alkyl Vancomycins", The Journal of Antibiotics, vol. XLII, No. 1, pp 63-72 (1989).

Nicolaou et al., "Chemistry, Biology, and Medicine of the Glycopeptide Antibiotics", Angew Chem. Int. Ed., 38, pp 2096-2152 (1999).

Pavlov et al., "A New Type of Chemical Modification of Glycopeptides Antibiotics: Aminomethylated Derivaties of Eremomycin and Their Antibacterial Activity", The Journal of Antibiotics, vol. 50, No. 6, pp 509-513 (1997).

Pavlov et al., Chemical Modification of Glycopeptide Antibiotics [VC1], Russian Journal of Bioorganic Chemistry, vol. 24, No. 9, pp 570-587(1998).

Pavlov et al., "Mono and Double Modified Teicoplanin Aglycon Derivatives on the Amino Acid No. 7; Structure-activity Relationship", The Journal of Antibiotics, vol. 51, No. 1, pp 73-78 (1998).

Pea et al., "High vancomycin dosage regimens required by intensive care unit patients cotreated with drugs to improve haemodynamics following cardiac surgical procedures", Journal of Antimicrobial Chemotherapy, 45, pp 329-335 (2000).

Uekama et al., "Protective effects of cyclodextrin sulphates against gentamicin-induced nephrotoxicity in the rat", J. Pharm. Pharmacol.., 45, pp 745-747 (1993).

Zhang et al., "A review of recent applications of cyclodextrins for drug discovery", Exp. Opin. Ther. Patents, 9(12), pp 1697-1717 (1999).

Toyoguchi et al., "Nephrotoxicity of Vancomycin and Durg Interaction Study with Cilastatin in Rabbits," Antimicrob. Agents Chemother., 1997, 41(9). 1985-1990.

PHARMACEUTICAL COMPOSITIONS CONTAINING A GLYCOPEPTIDE ANTIBIOTIC AND A CYCLODEXTRIN

CROSS-REFERENCE TO RELATED APPLICATIONS

This application is a continuation of U.S. application Ser. No. 09/846,893, filed May 1, 2001, now U.S. Pat. No. 6,858,584; which application claims the benefit of U.S. Provisional Application No. 60/201,178, filed 02 May 2000; and U.S. Provisional Applications Nos. 60/213,415; 60/213,410; 60/213,417; 60/213,146; 60/213,428, all filed 22 Jun. 2000; and U.S. Provisional Application No. 60/226,727, filed 18 Aug. 2000, which applications are incorporated herein by reference in their entirety.

BACKGROUND OF THE INVENTION

1. Field of the Invention

This invention is directed to novel pharmaceutical compositions comprising a cyclodextrin and a therapeutically effective amount of a glycopeptide antibiotic. This invention is also directed to methods for treating a bacterial disease in a mammal using such pharmaceutical compositions.

2. State of the Art

Glycopeptide antibiotics and lipidated derivatives thereof are well-known in the art (see *Glycopeptide Antibiotics*, edited by R. Nagarajan, Marcel Dekker, Inc. New York (1994)). These glycopeptide compounds are highly effective antibiotics for treating a wide variety of bacterial diseases in mammals. However, when administered to a mammal, some glycopeptide antibiotics exhibit undesirable properties, such as excessive tissue accumulation, nephrotoxicity, histamine release (Red Man Syndrome) and vascular irritation. Accordingly, a need exists for novel pharmaceutical compositions of glycopeptide antibiotics which reduce these undesired properties.

SUMMARY OF THE INVENTION

The present invention provides novel pharmaceutical compositions comprising a cyclodextrin and a therapeutically effective amount of a glycopeptide antibiotic. Surprisingly, when administered to a mammal, the pharmaceutical compositions of this invention exhibit one or more of the following properties (a) reduced tissue accumulation of the glycopeptide antibiotic, (b) reduced nephrotoxicity, (c) reduced histamine release (Red Man Syndrome) and (d) reduced vascular irritation, compared to a pharmaceutical composition which does not contain the cyclodextrin.

By reducing the undesirable effects of the glycopeptide (e.g. nephrotoxicity), administration of the glycopeptide in combination with a cyclodextrin increases the therapeutic window for the glycopeptide, and allows a greater amount to be administered.

Accordingly, in one of its composition aspects, this invention is directed to a pharmaceutical composition comprising a cyclodextrin and a therapeutically effective amount of a glycopeptide antibiotic, or a pharmaceutically acceptable salt thereof. This preferred composition can be in the form of a lyophilized powder or a sterilized powder.

In another one of its composition aspects, this invention is directed to a pharmaceutical composition comprising an aqueous cyclodextrin solution and a therapeutically effective amount of a glycopeptide antibiotic, or a pharmaceutically acceptable salt thereof.

In another preferred embodiment, the pharmaceutical composition comprises:

(a) a therapeutically effective amount of a glycopeptide antibiotic, or a pharmaceutically acceptable salt thereof;
(b) 1 to 40 weight percent of a cyclodextrin; and
(c) 60 to 99 weight percent of water, provided that the components of the composition total 100 weight percent.

Preferably, the cyclodextrin employed in the pharmaceutical compositions of this invention is hydroxypropyl-β-cyclodextrin or sulfobutyl ether β-cyclodextrin. More preferably, the cyclodextrin is hydroxypropyl-β-cyclodextrin. Preferably, the cyclodextrin will comprise up to about 90 weight percent, and typically about 1 to 40 weight percent; preferably, about 5 to 35 weight percent; more preferable, about 10 to 30 weight percent, of the formulation.

Preferably, the glycopeptide antibiotic employed in the pharmaceutical compositions of this invention is a lipidated glycopeptide antibiotic. Preferably, the glycopeptide antibiotic will be present in the pharmaceutical composition in a therapeutically effective amount.

In a preferred embodiment, the glycopeptide antibiotic employed in this invention is a compound of formula I

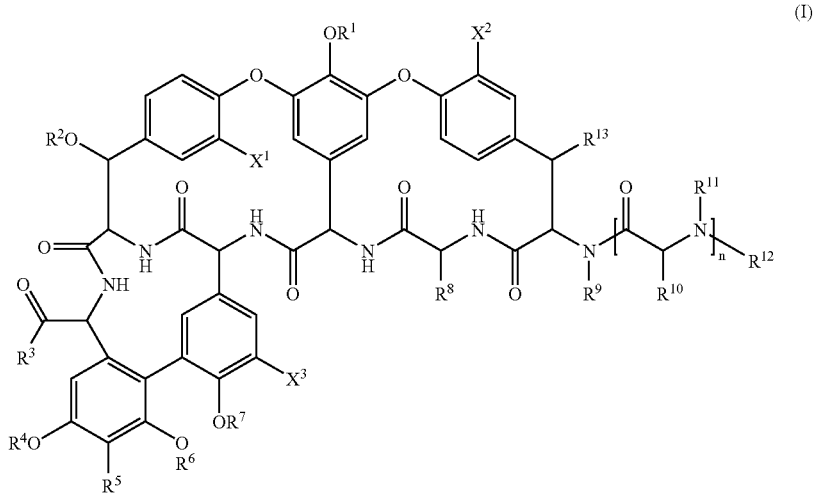

wherein:

$R^1$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —$R^a$—Y—$R^b$-$(Z)_x$; or $R^1$ is a saccharide group optionally substituted with —$R^a$—Y—$R^b$-$(Z)_x$, $R^f$, —C(O)$R^f$, or —C(O)—$R^a$—Y—$R^b$-$(Z)_x$;

$R^2$ is hydrogen or a saccharide group optionally substituted with —$R^a$—Y—$R^b$-$(Z)_x$, $R^f$, —C(O)$R^f$, or —C(O)—$R^a$—Y—$R^b$-$(Z)_x$;

$R^3$ is —$OR^c$, —$NR^cR^c$, —O—$R^a$—Y—$R^b$-$(Z)_x$, —$NR^c$—$R^a$—Y—$R^b$-$(Z)_x$, —$NR^cR^e$, or —O—$R^e$; or $R^3$ is a nitrogen-linked, oxygen-linked, or sulfur-linked substituent that comprises one or more phosphono groups;

$R^4$ is selected from the group consisting of hydrogen, alkyl, substituted alkyl, alkenyl, substituted alkenyl, alkynyl, substituted alkynyl, —$R^a$—Y—$R^b$-$(Z)_x$, —C(O)$R^d$ and a saccharide group optionally substituted with —$R^a$—Y—$R^b$-$(Z)_x$, $R^f$, —C(O)$R^f$, or —C(O)—$R^a$—Y—$R^b$-$(Z)_x$;

$R^5$ is selected from the group consisting of hydrogen, halo, —CH($R^c$)—$NR^cR^c$, —CH($R^c$)—$NR^cR^e$, —CH($R^c$)—$NR^c$—$R^a$—Y—$R^b$-$(Z)_x$, —CH($R^c$)—$R^x$, —CH($R^c$)—$NR^c$—$R^a$—C(=O)—$R^x$, and a substituent that comprises one or more phosphono groups;

$R^6$ is selected from the group consisting of hydrogen, alkyl, substituted alkyl, alkenyl, substituted alkenyl, alkynyl, substituted alkynyl, —$R^a$—Y—$R^b$-$(Z)_x$, —C(O)$R^d$ and a saccharide group optionally substituted with —$NR^c$—$R^a$—Y—$R^b$-$(Z)_x$, or $R^5$ and $R^6$ can be joined, together with the atoms to which they are attached, form a heterocyclic ring optionally substituted with —$NR^c$—$R^a$—Y—$R^b$-$(Z)_x$;

$R^7$ is selected from the group consisting of hydrogen, alkyl, substituted alkyl, alkenyl, substituted alkenyl, alkynyl, substituted alkynyl, —$R^a$—Y—$R^b$-$(Z)_x$, and —C(O)$R^d$;

$R^8$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;

$R^9$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;

$R^{10}$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic; or $R^8$ and $R^{10}$ are joined to form —$Ar^1$—O—$Ar^2$—, where $Ar^1$ and $Ar^2$ are independently arylene or heteroarylene;

$R^{11}$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic, or $R^{10}$ and $R^{11}$ are joined, together with the carbon and nitrogen atoms to which they are attached, to form a heterocyclic ring;

$R^{12}$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic, —C(O)$R^d$, —C(NH)$R^d$, —C(O)$NR^cR^c$, —C(O)$OR^d$, —C(NH)$NR^cR^c$ and —$R^a$—Y—$R^b$-$(Z)_x$, or $R^{11}$ and $R^{12}$ are joined, together with the nitrogen atom to which they are attached, to form a heterocyclic ring;

$R^{13}$ is selected from the group consisting of hydrogen or —$OR^{14}$;

$R^{14}$ is selected from hydrogen, —C(O)$R^d$ and a saccharide group;

each $R^a$ is independently selected from the group consisting of alkylene, substituted alkylene, alkenylene, substituted alkenylene, alkynylene and substituted alkynylene;

each $R^b$ is independently selected from the group consisting of a covalent bond, alkylene, substituted alkylene, alkenylene, substituted alkenylene, alkynylene and substituted alkynylene, provided $R^b$ is not a covalent bond when Z is hydrogen;

each $R^c$ is independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —C(O)$R^d$;

each $R^d$ is independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;

$R^e$ is a saccharide group;

each $R^f$ is independently alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, or heterocyclic;

$R^x$ is an N-linked amino saccharide or an N-linked heterocycle;

$X^1$, $X^2$ and $X^3$ are independently selected from hydrogen or chloro;

each Y is independently selected from the group consisting of oxygen, sulfur, —S—S—, —$NR^c$—, —S(O)—, —$SO_2$—, —$NR^cC(O)$—, —$OSO_2$—, —OC(O)—, —$NR^cSO_2$—, —C(O)$NR^c$—, —C(O)O—, —$SO_2NR^c$—, —$SO_2O$—, —P(O)(O$R^c$)O—, —P(O)(O$R^c$)$NR^c$—, —OP(O)(O$R^c$)O—, —OP(O)(O$R^c$)$NR^c$—, —OC(O)O—, —$NR^cC(O)O$—, —$NR^cC(O)NR^c$—, —OC(O)$NR^c$—, —C(=O)—, and —$NR^cSO_2NR^c$—;

each Z is independently selected from hydrogen, aryl, cycloalkyl, cycloalkenyl, heteroaryl and heterocyclic;

n is 0, 1 or 2; and x is 1 or 2;

or a pharmaceutically acceptable salt, stereoisomer, or prodrug thereof.

Preferably, $R^1$ is a saccharide group optionally substituted with —$R^a$—Y—$R^b$-$(Z)_x$, $R^f$, —C(O)$R^f$, or —C(O)—$R^a$—Y—$R^b$-(Z). More preferably $R^1$ is an amino saccharide group substituted on the saccharide nitrogen with —$CH_2CH_2$—NH—$(CH_2)_9CH_3$; —$CH_2CH_2CH_2$—NH—$(CH_2)_8CH_3$; —$CH_2CH_2CH_2CH_2$—NH—$(CH_2)_7CH_3$; —$CH_2CH_2$—$NHSO_2$—$(CH_2)_9CH_3$; —$CH_2CH_2$—$NHSO_2$—$(CH_2)_{11}CH_3$; —$CH_2CH_2$—S—$(CH_2)_8CH_3$; —$CH_2CH_2$—S—$(CH_2)_9CH_3$; —$CH_2CH_2$—S—$(CH_2)_{10}CH_3$; —$CH_2CH_2CH_2$—S—$(CH_2)_8CH_3$; —$CH_2CH_2CH_2$—S—$(CH_2)_9CH_3$; —$CH_2CH_2$—S—$(CH_2)_3$—CH=CH—$(CH_2)_4CH_3$ (trans); —$CH_2CH_2CH_2CH_2$—S—$(CH_2)_7CH_3$; —$CH_2CH_2$—S(O)—$(CH_2)_9CH_3$; —$CH_2CH_2$—S—$(CH_2)_6Ph$; —$CH_2CH_2$—S—$(CH_2)_8Ph$; —$CH_2CH_2CH_2$—S—$(CH_2)_8$ Ph; —$CH_2CH_2$—NH—$CH_2$-4-(4-Cl-Ph)-Ph; —$CH_2CH_2$—NH—$CH_2$-4-[(4—$(CH_3)_2$CHCH$_2$—]-Ph; —$CH_2CH_2$—NH—$CH_2$-4-(4-CF$_3$-Ph)-Ph; —$CH_2CH_2$—S—$CH_2$-4-(4-Cl-Ph)-Ph; —$CH_2CH_2$—S(O)—$CH_2$-4-(4-Cl-Ph)-Ph; —$CH_2CH_2CH_2$—S—$CH_2$-4-(4-Cl-Ph)-Ph; —$CH_2CH_2CH_2$—S(O)—$CH_2$-4-(4-Cl-Ph)-Ph; —$CH_2CH_2CH_2$—S—$CH_2$-4-[3,4-di-Cl-PhCH$_2$O—)-Ph;

—CH₂CH₂—NHSO₂—CH₂-4-[4-(4-Ph)-Ph]-Ph;
—CH₂CH₂CH₂—NHSO₂—CH₂-4-(4-Cl-Ph)-Ph;
—CH₂CH₂CH₂—NHSO₂—CH₂-4-(Ph-C≡C—)-Ph;
—CH₂CH₂CH₂—NHSO₂-4-(4-Cl-Ph)-Ph;
—CH₂CH₂CH₂—NHSO₂-4-(naphth- 2-yl)-Ph; or —CH₂-4-(4-Cl-Ph)-Ph. More preferably R¹ can also be an amino saccharide group substituted on the saccharide nitrogen with 4-(4-chlorophenyl)benzyl or 4-(4-chlorobenzyloxy)benzyl.

More preferably, R¹ is a saccharide group of the formula:

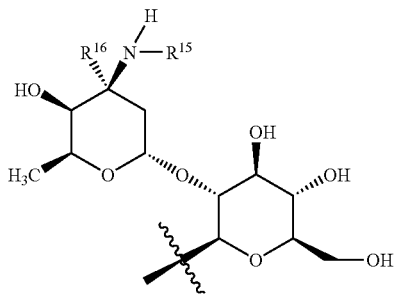

wherein R¹⁵ is —Rᵃ—Y—Rᵇ-(Z)ₓ, Rᶠ, —C(O)Rᶠ, or —C(O)—Rᵃ—Y—Rᵇ-(Z)ₓ; and R¹⁶ is hydrogen or methyl.

Preferably, R¹⁵ is —CH₂CH₂—NH—(CH₂)₉CH₃; —CH₂CH₂CH₂—NH—(CH₂)₈CH₃; —CH₂CH₂CH₂CH₂—NH—(CH₂)₇CH₃; —CH₂CH₂—NHSO₂—(CH₂)₉CH₃; —CH₂CH₂—NHSO₂—(CH₂)₁₁CH₃; —CH₂CH₂—S—(CH₂)₈CH₃; —CH₂CH₂—S—(CH₂)₉CH₃; —CH₂CH₂—S—(CH₂)₁₀CH₃; —CH₂CH₂CH₂—S—(CH₂)₈CH₃; —CH₂CH₂CH₂—S—(CH₂)₉CH₃; —CH₂CH₂CH₂—S—(CH₂)₃—CH=CH—(CH₂)₄CH₃ (trans); —CH₂CH₂CH₂CH₂—S—(CH₂)₇CH₃; —CH₂CH₂—S(O)—(CH₂)₉CH₃; —CH₂CH₂—S—(CH₂)₆Ph; —CH₂CH₂—S—(CH₂)₈Ph; —CH₂CH₂CH₂—S—(CH₂)₈Ph; —CH₂CH₂—NH—CH₂-4-(4-Cl-Ph)-Ph; —CH₂CH₂—NH—CH₂-4-[4-(CH₃)₂CHCH₂—]-Ph; —CH₂CH₂—NH—CH₂-4-(4-CF₃-Ph)-Ph; —CH₂CH₂—S—CH₂-4-(4-Cl-Ph)-Ph; —CH₂CH₂—S(O)—CH₂-4-(4-Cl-Ph)-Ph; —CH₂CH₂CH₂—S—CH₂-4-(4-Cl-Ph)-Ph; —CH₂CH₂CH₂—S(O)—CH₂-4-(4-Cl-Ph)-Ph; —CH₂CH₂CH₂—S—CH₂-4-[3,4-di-Cl-PhCH₂O—)-Ph; —CH₂CH₂—NHSO₂—CH₂-4-[4-(4-Ph)-Ph]-Ph; —CH₂CH₂CH₂—NHSO₂—CH₂-4-(4-Cl-Ph)-Ph; —CH₂CH₂CH₂—NHSO₂—CH₂-4-(Ph-C≡C—)-Ph; —CH₂CH₂CH₂—NHSO₂-4-(4-Cl-Ph)-Ph; —CH₂CH₂CH₂—NHSO₂-4-(naphth-2-yl)-Ph; or —CH₂-4-(4-Cl-Ph)-Ph.

Preferably, R¹⁵ can also be 4-(4-chlorophenyl)benzyl or 4-(4-chlorobenzyloxy)benzyl.

Preferably, R² is hydrogen.

Preferably, R³ is —ORᶜ; —NRᶜRᶜ. More preferably, R³ is —OH; —NH—(CH₂)₃—N(CH₃)₂; N-(D-glucosamine); —NHCH(CO₂CH₃)CH₂CO₂CH₃; —NH(CH₂)₃-(morpholin-4-yl); —NH(CH₂)₃—NH(CH₂)₂CH₃ ; —NH(CH₂-piperidin-1-yl; —NH(CH₂)₄NHC(N)NH₂; —NH(CH₂)₂—N⁺(CH₃)₃; —NHCH(COOH)(CH₂)₃NHC(N)NH₂; —NH—[CH₂CH₂CH₂—NH—]₃—H; —N[(CH₂)₃N(CH₃)₂]₂; —NH(CH₂)₃-imidazol-1-yl; —NHCH₂-4-pyridyl; —NH(CH₂)₃CH₃; —NH(CH₂)₂OH; —NH(CH₂)₅OH; —NH(CH₂)₂OCH₃; —NHCH₂-tetrahydrofuran-2-yl; —N[(CH₂)₂OH]₂; —NH(CH₂)₂N[(CH₂)₂OH]₂; —NHCH₂COOH; —NHCH(COOH)CH₂OH; —NH(CH₂)₂COOH; N-(glucamine); —NH(CH₂)₂COOH; —NH(CH₂)₃SO₃H; —NHCH(COOH)(CH₂)₂NH₂; —NHCH(COOH)(CH₂)₃NH₂; —NHCH(COOH)CH₂CO₂(CH₂)₃—N⁺(CH₃)₃; —NHCH(COOH)CH₂CO₂(CH₂)₂C(O)—N(CH₃)₂; —NHCH(COOH)CH₂CO₂(CH₂)₃-morpholin-4-yl; —NHCH(COOH)CH₂CO₂(CH₂)₂OC(O)C(CH₃)₃; —NHCH(CH₂COOH)CO₂(CH₂)₃—N⁺(CH₃)₃; —NHCH(CH₂COOH)CO₂(CH₂)₂C(O)N(CH₃)₂; —NHCH(CH₂COOH)CO₂(CH₂)₂-morpholin-4-yl; —NHCH(CH₂COOH)CO₂(CH₂)₂OC(O)C(CH₃)₃; —NHCH(COOH)CH₂CO₂CH₃; —NHCH(CH₂COOH)CO₂(CH₂)₂N(CH₃)₂; —NHCH(COOH)CH₂CO₂CH₂C(O)N(CH₃)₂; —NHCH(CH₂COOH)CO₂CH₂C(O)N(CH₃)₂; —NHCH(CH₂COOH)CO₂CH₃; —NH(CH₂)₃N(CH₃)₂; —NHCH₂CH₂CO₂CH₃; —NHCH[CH₂CO₂CH₂C(O)N(CH₃)₂]CO₂CH₂—C(O)—N(CH₃)₂; —NHCH₂CO₂CH₃; —N-(methyl3-amino-3-deoxyaminopyranoside); —N-(methyl3-amino-2,3,6-trideoxyhexopyranoside); —N-(2-amino-2-deoxy-6-(dihydrogenphosphate)glucopyranose; —N-(2-amino-2-deoxygluconic acid); —NH(CH₂)₄COOH; —N—(N—CH₃-D-glucamine; —NH(CH₂)₆COOH; —O(D-glucose); —NH(CH₂)₃OC(O)CH(NH₂)CH₃; —NH(CH₂)₄CH(C(O)-2-HOOC-pyrrolidin-1-yl)NHCH(COOH)—CH₂CH₂Ph (S,S isomer); —NH—CH₂CH₂—NH—(CH₂)₉CH₃; —NH(CH₂)₂C(O)CH₂C(O)N(CH₃)₂. Still more preferably, R³ is —OH.

Preferably, R⁴, R⁶ and R⁷ are each independently selected from hydrogen or —C(O)Rᵈ. More preferably, R⁴, R⁶ and R⁷ are each hydrogen.

Preferably, R⁵ is hydrogen, —CH₂—NHRᶜ, —CH₂—NRᶜRᵉ, —CH₂—NH—Rᵃ—Y—Rᵇ-(Z)ₓ, or a substituent comprising one or two phosphono groups. When R⁵ is phosphono-containing substituent, R⁵ is preferably a group of the formula —CH₂—NH—Rᵃ—P(O)(OH)₂, where Rᵃ is as defined herein. In this formula, Rᵃ is preferably an alkylene group. Particularly preferred R⁵ substituents include N-(phoshonomethyl)aminomethyl; N-(2-hydroxy-2-phosphonoethyl)aminomethyl; N-carboxymethyl-N-(2-phosphonoethyl)aminomethyl; N,N-bis(phosphonomethyl)aminomethyl; N-(3-phosphonopropyl)aminomethyl; and the like.

Preferably, when R⁵ is not a phosphono-containing substituent, R⁵ is hydrogen, —CH₂—NHRᶜ, —CH₂—NRᶜRᵉ or —CH₂—NH—Rᵃ—Y—Rᵇ-(Z)ₓ. R⁵ can also preferably be hydrogen; —CH₂—N—(N—CH₃-D-glucamine); —CH₂—NH—CH₂CH₂—NH—(CH₂)₉CH₃; —CH₂—NH—CH₂CH₂—NHC(O)—(CH₂)₃COOH; —CH₂—NH—(CH₂)₉ CH₃; —CH₂—NH—CH₂CH₂—COOH; —CH₂—NH—(CH₂)₅COOH; —CH₂-(morpholin-4-yl); —CH₂—NH—CH₂CH₂—O—CH₂CH₂OH; —CH₂—NH—CH₂CH(OH)—CH₂OH; —CH₂—N[CH₂CH₂OH]₂; —CH₂—NH—(CH₂)₃—N(CH₃)₂; —CH₂—N[(CH₂)₃—N(CH₃)₂]₂; —CH₂—NH—(CH₂)₃-(imidazol-1-yl); —CH₂—NH—(CH₂)₃-(morpholin-4-yl); —CH₂—NH—(CH₂)₄—NHC(NH)NH₂; —CH₂—N-(2-amino-2-deoxygluconic acid); —CH₂—NH—CH₂CH₂—NH—(CH₂)₁₁CH₃; —CH₂—NH—CH(COOH)CH₂COOH; —CH₂—NH—CH₂CH₂—NHSO₂—(CH₂)₇CH₃; —CH₂—NH—CH₂CH₂—NHSO₂—(CH₂)₈CH₃; —CH₂—NH—CH₂CH₂—NHSO₂—(CH₂)₉CH₃; —CH₂—NH—CH₂CH₂—NHSO₂—(CH₂)₁₁CH₃; —CH₂—NH—CH₂CH₂—NH—(CH₂)₇CH₃; —CH₂—NH—CH₂CH₂—O—CH₂CH₂OH; —CH₂—NH—CH₂CH₂C(O)—N-(D-glucosamine); —CH₂—NH-(6-oxo-[1,3]oxazinan-3-yl); —CH₂—NH—CH₂CH₂—S—(CH₂)₇CH₃; —CH₂—NH—CH₂CH₂—S—(CH₂)₈CH₃; —CH₂—NH—CH₂CH₂—S—(CH₂)₉CH₃; —CH₂—NH—CH₂CH₂—S—(CH₂)₁₁CH₃; —CH₂—NH—CH₂CH₂—S—(CH₂)₆Ph; —CH₂—NH—CH₂CH₂—

S—(CH$_2$)$_8$Ph; —CH$_2$—NH—CH$_2$CH$_2$— S—(CH$_2$)$_{10}$Ph; —CH$_2$—NH—CH$_2$CH$_2$—S—CH$_2$-(4-(4-CF$_3$-Ph)Ph); —CH$_2$—NH—CH$_2$CH$_2$—NH—(CH$_2$)$_{11}$CH$_3$; or —CH$_2$—NH—(CH$_2$)$_5$—COOH. More preferably, R$^5$ is hydrogen.

Preferably, R$^8$ is —CH$_2$C(O)NH$_2$, —CH$_2$COOH, benzyl, 4-hydroxyphenyl or 3-choloro-4-hydroxyphenyl.

Preferably, R$^9$ is hydrogen or alkyl.

Preferably, R$^{10}$ is alkyl or substituted alkyl. More preferably, R$^{10}$ is the side-chain of a naturally occurring amino acid, such as isobutyl.

Preferably, R$^{11}$ is hydrogen or alkyl.

Preferably, R$^{12}$ is hydrogen, alkyl, substituted alkyl or —C(O)R$^d$. R$^{12}$ can also preferably be hydrogen; —CH$_2$COOH; —CH$_2$—[CH(OH)]$_5$CH$_2$OH; —CH$_2$CH(OH)CH$_2$OH; —CH$_2$CH$_2$NH$_2$; —CH$_2$C(O)OCH$_2$CH$_3$; —CH$_2$-(2-pyridyl); —CH$_2$—[CH(OH)]$_4$COOH; —CH$_2$-(3-carboxyphenyl); (R)—C(O)CH(NH$_2$)(CH$_2$)$_4$NH$_2$; —C(O)Ph; —C(O)CH$_2$NHC(O)CH$_3$; E-CH$_2$CH$_2$—S—(CH$_2$)$_3$CH=CH(CH$_2$)$_4$CH$_3$; or —C(O)CH$_3$.

Preferably, X$^1$ and X$^2$ are each chloro.

Preferably, X$^3$ is hydrogen.

Preferably, each Y is independently selected from the group consisting of oxygen, sulfur, —S—S—, —NR$^c$—, —S(O)—, —SO$_2$—, —NR$^c$C(O)—, —OSO$_2$—, —OC(O)—, —NR$^c$SO$_2$—, —C(O)NR$^c$—, —C(O)O—, —SO$_2$NR$^c$—, —SO$_2$O—, —P(O)(OR$^c$)O—, —P(O)(OR$^c$)NR$^c$—, —OP(O)(OR$^c$)O—, —OP(O)(OR$^c$)NR$^c$—, —OC(O)O—, —NR$^c$C(O)O—, —NR$^c$C(O)NR$^c$—, —OC(O)NR$^c$—, and —NR$^c$SO$_2$NR$^c$—. More preferably, Y is oxygen, sulfur or —NR$^c$—.

Preferably, n is 0 or 1, and more preferably, n is 1.

Another preferred group of glycopeptide antibiotics for use in this invention are those of formula II:

wherein:

R$^{19}$ is hydrogen;

R$^{20}$ is —R$^a$—Y—R$^b$-(Z)$_x$, R$^f$, —C(O)R$^f$, or —C(O)—R$^a$—Y—R$^b$-(Z)$_x$; and R$^a$, Y, R$^b$, Z, x, R$^f$, R$^3$, and R$^5$ have any of the values or preferred values described herein;

or a pharmaceutically acceptable salt, stereoisomer, or prodrug thereof.

Preferably, R$^{20}$ is —CH$_2$CH$_2$—NH—(CH$_2$)$_9$CH$_3$; —CH$_2$CH$_2$CH$_2$—NH—(CH$_2$)$_8$CH$_3$; —CH$_2$CH$_2$CH$_2$CH$_2$—NH—(CH$_2$)$_7$CH$_3$; —CH$_2$CH$_2$—NHSO$_2$—(CH$_2$)$_9$CH$_3$; —CH$_2$CH$_2$—NHSO$_2$—(CH$_2$)$_{11}$CH$_3$; —CH$_2$CH$_2$—S—(CH$_2$)$_8$CH$_3$; —CH$_2$CH$_2$—S—(CH$_2$)$_9$CH$_3$; —CH$_2$CH$_2$—S—(CH$_2$)$_{10}$CH$_3$; —CH$_2$CH$_2$CH$_2$—S—(CH$_2$)$_8$CH$_3$; —CH$_2$CH$_2$CH$_2$—S—(CH$_2$)$_9$CH$_3$; —CH$_2$CH$_2$—S—(CH$_2$)$_3$—CH=CH—(CH$_2$)$_4$CH$_3$ (trans); —CH$_2$CH$_2$CH$_2$CH$_2$—S—(CH$_2$)$_7$CH$_3$; —CH$_2$CH$_2$—S(O)—(CH$_2$)$_9$CH$_3$; —CH$_2$CH$_2$—S—(CH$_2$)$_6$Ph; —CH$_2$CH$_2$—S—(CH$_2$)$_8$Ph; —CH$_2$CH$_2$CH$_2$—S—(CH$_2$)$_8$Ph; —CH$_2$CH$_2$—NH—CH$_2$-4-(4-Cl-Ph)-Ph; —CH$_2$CH$_2$—NH—CH$_2$-4-[4-(CH$_3$)$_2$CHCH$_2$—]-Ph; —CH$_2$CH$_2$—NH—CH$_2$-4-(4-CF$_3$-Ph)-Ph; —CH$_2$CH$_2$—S—CH$_2$-4-(4-Cl-Ph)-Ph; —CH$_2$CH$_2$—S(O)—CH$_2$-4-(4-Cl-Ph)-Ph; —CH$_2$CH$_2$CH$_2$—S—CH$_2$-4-(4-Cl-Ph)-Ph; —CH$_2$CH$_2$CH$_2$—S(O)—CH$_2$-4-(4-Cl-Ph)-Ph; —CH$_2$CH$_2$CH$_2$—S—CH$_2$-4-[3,4-di-Cl-PhCH$_2$O—)-Ph; —CH$_2$CH$_2$—NHSO$_2$—CH$_2$-4-[4-(4-Ph)-Ph]-Ph; —CH$_2$CH$_2$CH$_2$—NHSO$_2$—CH$_2$-4-(4-Cl-Ph)-Ph; —CH$_2$CH$_2$CH$_2$—NHSO$_2$—CH$_2$-4-(Ph-C≡C—)-Ph; —CH$_2$CH$_2$CH$_2$—NHSO$_2$-4-(4-Cl-Ph)-Ph; —CH$_2$CH$_2$CH$_2$—NHSO$_2$-4-(naphth-2-yl)-Ph; or —CH$_2$-4-(4-Cl-Ph)-Ph. Preferably, R$^{20}$ can also be 4-(4-chlorophenyl)benzyl or 4-(4-chlorobenzyloxy)benzyl.

(II)

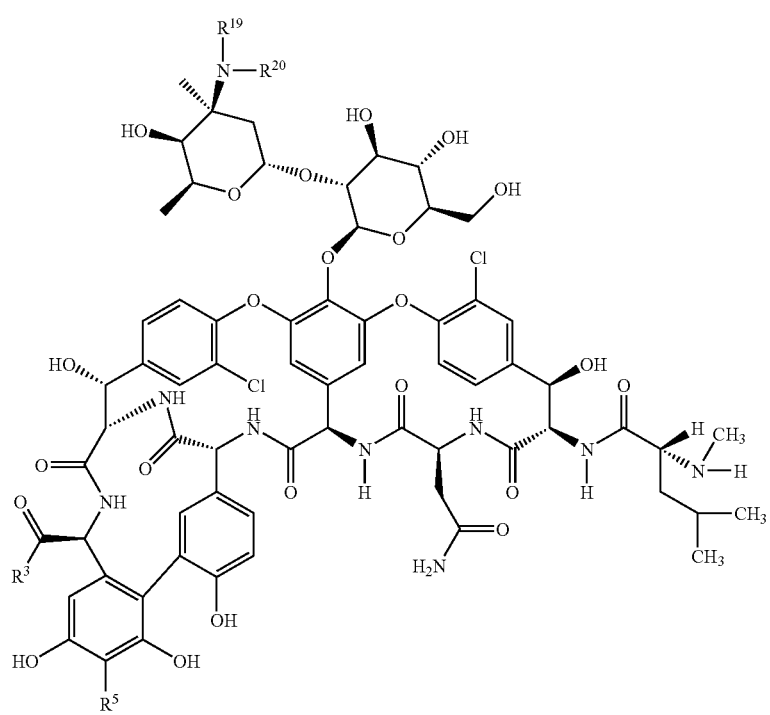

Still another preferred group of glycopeptide antibiotics for use in this invention are derivatives of the glycopeptide antibiotic A82846B (also known as chloroorienticin A oy LY264826). See for example R. Nagarajan et al., *J. Org. Chem.*, 1988, 54, 983–986; and N. Tsuji et al., *J. Antibiot.*, 1988, 41, 819–822. The structure of this glycopeptide is similar to vancomycin, except A82846B contains an additional amino sugar (i.e. 4-epi-vancosamine attached at the $R^2$ position in formula I.) and further contains 4-epi-vancosamine in place of vancosamine in the disaccharide moiety attached at the $R^1$ position in formula I. For example, a preferred group of compounds are N-alkylated derivatives of A82846B; or a pharmaceutically acceptable salt thereof. For example, a preferred compound is a derivative of A82846B having a 4-(4-chlorophenyl)benzyl group or a 4-(4-chlorobenzyloxy)benzyl group attached at the amino group of the 4-epi-vancosamine of the disaccharide moiety.

The pharmaceutical compositions of this invention are highly effective for treating bacterial diseases. Accordingly, in one of its method aspects, this invention is also directed to a method of treating a bacterial disease in a mammal, the method comprising administering to the mammal a pharmaceutical composition comprising cyclodextrin and a therapeutically effective amount of a glycopeptide antibiotic, or a pharmaceutically acceptable salt thereof. This method includes each of the preferred embodiments for the pharmaceutical composition described herein.

In another of its method aspects, this invention is directed to a method for reducing tissue accumulation of a glycopeptide antibiotic when administered to a mammal, the method comprising administering the glycopeptide antibiotic to the mammal in a pharmaceutical composition comprising a cyclodextrin and a therapeutically effective amount of the glycopeptide antibiotic, or a pharmaceutically acceptable salt thereof.

This invention is also directed to a method for reducing nephrotoxicity produced by a glycopeptide antibiotic when administered to a mammal, the method comprising administering the glycopeptide antibiotic to the mammal in a pharmaceutical composition comprising a cyclodextrin and a therapeutically effective amount of the glycopeptide antibiotic, or a pharmaceutically acceptable salt thereof.

This invention is also directed to a method for reducing histamine release produced by a glycopeptide antibiotic when administered to a mammal, the method comprising administering the glycopeptide antibiotic to the mammal in a pharmaceutical composition comprising a cyclodextrin and a therapeutically effective amount of the glycopeptide antibiotic, or a pharmaceutically acceptable salt thereof.

This invention is also directed to a method for reducing vascular irritation produced by a glycopeptide antibiotic when administered to a mammal, the method comprising administering the glycopeptide antibiotic to the mammal in a pharmaceutical composition comprising a cyclodextrin and a therapeutically effective amount of the glycopeptide antibiotic, or a pharmaceutically acceptable salt thereof.

According to one embodiment, the above described methods of the invention can be carried out by administering the glycopeptide antibiotic to the mammal in a pharmaceutical composition comprising an aqueous cyclodextrin solution and a therapeutically effective amount of the glycopeptide antibiotic.

Preferably, according to the methods of the invention, the weight ratio of cyclodextrin to glycopeptide will range from about 0.5:1 to 20:1, and more preferably, from about 1:1 to about 10:1.

DETAILED DESCRIPTION OF THE INVENTION

This invention relates to novel pharmaceutical compositions and to methods of treating bacterial diseases in a mammal using such compositions. When describing the compounds, compositions and methods of this invention, the following terms have the following meanings, unless otherwise indicated.

Definitions

The term "alkyl" refers to a monoradical branched or unbranched saturated hydrocarbon chain preferably having from 1 to 40 carbon atoms, more preferably 1 to 10 carbon atoms, and even more preferably 1 to 6 carbon atoms. This term is exemplified by groups such as methyl, ethyl, n-propyl, iso-propyl, n-butyl, iso-butyl, n-hexyl, n-decyl, tetradecyl, and the like.

The term "substituted alkyl" refers to an alkyl group as defined above, having from 1 to 8 substituents, preferably 1 to 5 substituents, and more preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl, —$SO_3H$, guanido, and —$SO_2$-heteroaryl.

The term "alkylene" refers to a diradical of a branched or unbranched saturated hydrocarbon chain, preferably having from 1 to 40 carbon atoms, preferably 1–10 carbon atoms, more preferably 1–6 carbon atoms. This term is exemplified by groups such as methylene (—$CH_2$—), ethylene (—$CH_2CH_2$—), the propylene isomers (e.g., —$CH_2CH_2CH_2$— and —$CH(CH_3)CH_2$—) and the like.

The term "substituted alkylene" refers to an alkylene group, as defined above, having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —$SO_2$-heteroaryl, —$SO_2$-alkyl, —$SO_2$-substituted alkyl, —$SO_2$-aryl and —$SO_2$-heteroaryl. Additionally, such substituted alkylene groups include those where 2 substituents on the alkylene group are fused to form one or more cycloalkyl, substituted cycloalkyl, cycloalkenyl, substituted cycloalkenyl, aryl, heterocyclic or heteroaryl groups fused to the alkylene group. Preferably such fused groups contain from 1 to 3 fused ring structures. Additionally, the term substituted alkylene includes alkylene groups in which from 1 to 5 of the alkylene carbon atoms are replaced with oxygen, sulfur or —NR— where R is hydrogen or alkyl. Examples of substituted alkylenes are chloromethylene (—CH(Cl)—), aminoethylene (—CH($NH_2$)$CH_2$—), 2-carboxypropylene isomers (—$CH_2$CH($CO_2$H)$CH_2$—), ethoxyethyl (—$CH_2CH_2$O—$CH_2CH_2$—) and the like.

The term "alkaryl" refers to the groups-alkylene-aryl and -substituted alkylene-aryl where alkylene, substituted alkylene and aryl are defined herein. Such alkaryl groups are exemplified by benzyl, phenethyl and the like.

The term "alkoxy" refers to the groups alkyl-O—, alkenyl-O—, cycloalkyl-O—, cycloalkenyl-O—, and alkynyl-O—, where alkyl, alkenyl, cycloalkyl, cycloalkenyl, and alkynyl are as defined herein. Preferred alkoxy groups are alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkylalkoxy" refers to the groups-alkylene-O-alkyl, alkylene-O-substituted alkyl, substituted alkylene-O-alkyl and substituted alkylene-O-substituted alkyl wherein alkyl, substituted alkyl, alkylene and substituted alkylene are as defined herein. Preferred alkylalkoxy groups are alkylene-O-alkyl and include, by way of example, methylenemethoxy (—CH$_2$OCH$_3$), ethylenemethoxy (—CH$_2$CH$_2$OCH$_3$), n-propylene-iso-propoxy (—CH$_2$CH$_2$CH$_2$OCH(CH$_3$)$_2$), methylene-t-butoxy (—CH$_2$—O—C(CH$_3$)$_3$) and the like.

The term "alkylthioalkoxy" refers to the group-alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein. Preferred alkylthioalkoxy groups are alkylene-S-alkyl and include, by way of example, methylenethiomethoxy (—CH$_2$SCH$_3$), ethylenethiomethoxy (—CH$_2$CH$_2$SCH$_3$), n-propylene-iso-thiopropoxy (—CH$_2$CH$_2$CH$_2$SCH(CH$_3$)$_2$), methylene-t-thiobutoxy (—CH$_2$SC(CH$_3$)$_3$) and the like.

The term "alkenyl" refers to a monoradical of a branched or unbranched unsaturated hydrocarbon group preferably having from 2 to 40 carbon atoms, more preferably 2 to 10 carbon atoms and even more preferably 2 to 6 carbon atoms and having at least 1 and preferably from 1–6 sites of vinyl unsaturation. Preferred alkenyl groups include ethenyl (—CH=CH$_2$), n-propenyl (—CH$_2$CH=CH$_2$), iso-propenyl (—C(CH$_3$)=CH$_2$), and the like.

The term "substituted alkenyl" refers to an alkenyl group as defined above having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "alkenylene" refers to a diradical of a branched or unbranched unsaturated hydrocarbon group preferably having from 2 to 40 carbon atoms, more preferably 2 to 10 carbon atoms and even more preferably 2 to 6 carbon atoms and having at least 1 and preferably from 1–6 sites of vinyl unsaturation. This term is exemplified by groups such as ethenylene (—CH=CH—), the propenylene isomers (e.g., —CH$_2$CH=CH— and —C(CH$_3$)=CH—) and the like.

The term "substituted alkenylene" refers to an alkenylene group as defined above having from 1 to 5 substituents, and preferably from 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. Additionally, such substituted alkenylene groups include those where 2 substituents on the alkenylene group are fused to form one or more cycloalkyl, substituted cycloalkyl, cycloalkenyl, substituted cycloalkenyl, aryl, heterocyclic or heteroaryl groups fused to the alkenylene group.

The term "alkynyl" refers to a monoradical of an unsaturated hydrocarbon preferably having from 2 to 40 carbon atoms, more preferably 2 to 20 carbon atoms and even more preferably 2 to 6 carbon atoms and having at least 1 and preferably from 1–6 sites of acetylene (triple bond) unsaturation. Preferred alkynyl groups include ethynyl (—C≡CH), propargyl (—CH$_2$C≡CH) and the like.

The term "substituted alkynyl" refers to an alkynyl group as defined above having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "alkynylene" refers to a diradical of an unsaturated hydrocarbon preferably having from 2 to 40 carbon atoms, more preferably 2 to 10 carbon atoms and even more preferably 2 to 6 carbon atoms and having at least 1 and preferably from 1–6 sites of acetylene (triple bond) unsaturation. Preferred alkynylene groups include ethynylene (—C≡C—), propargylene (—CH$_2$C≡C—) and the like.

The term "substituted alkynylene" refers to an alkynylene group as defined above having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl The term "acyl" refers to the groups HC(O)—, alkyl-C(O)—, substituted alkyl-C(O)—, cycloalkyl-C(O)—, substituted cycloalkyl-C(O)—, cycloalkenyl-C(O)—, substituted cycloalkenyl-C(O)—, aryl-C(O)—, heteroaryl-C(O)— and heterocyclic-C(O)— where alkyl, substituted alkyl, cycloalkyl, substituted cycloalkyl, cycloalkenyl, substituted cycloalkenyl, aryl, heteroaryl and heterocyclic are as defined herein.

The term "acylamino" or "aminocarbonyl" refers to the group —C(O)NRR where each R is independently hydrogen, alkyl, substituted alkyl, aryl, heteroaryl, heterocyclic or where both R groups are joined to form a heterocyclic group (e.g., morpholino) wherein alkyl, substituted alkyl, aryl, heteroaryl and heterocyclic are as defined herein.

The term "aminoacyl" refers to the group —NRC(O)R where each R is independently hydrogen, alkyl, substituted alkyl, aryl, heteroaryl, or heterocyclic wherein alkyl, substituted alkyl, aryl, heteroaryl and heterocyclic are as defined herein.

The term "aminoacyloxy" or "alkoxycarbonylamino" refers to the group —NRC(O)OR where each R is independently hydrogen, alkyl, substituted alkyl, aryl, heteroaryl, or heterocyclic wherein alkyl, substituted alkyl, aryl, heteroaryl and heterocyclic are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclic-C(O)O— wherein alkyl, substituted alkyl, cycloalkyl, substituted cycloalkyl, aryl, heteroaryl, and heterocyclic are as defined herein.

The term "aryl" refers to an unsaturated aromatic carbocyclic group of from 6 to 20 carbon atoms having a single ring (e.g., phenyl) or multiple condensed (fused) rings, wherein at least one ring is aromatic (e.g., naphthyl, dihydrophenanthrenyl, fluorenyl, or anthryl). Preferred aryls include phenyl, naphthyl and the like.

Unless otherwise constrained by the definition for the aryl substituent, such aryl groups can optionally be substituted with from 1 to 5 substituents, preferably 1 to 3 substituents, selected from the group consisting of acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxy, carboxyalkyl, cyano, halo, nitro, heteroaryl, heteroaryloxy, heterocyclic, heterocyclooxy, aminoacyloxy, oxyacylamino, sulfonamide, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl. Preferred aryl substituents include alkyl, alkoxy, halo, cyano, nitro, trihalomethyl, and thioalkoxy.

The term "aryloxy" refers to the group aryl-O— wherein the aryl group is as defined above including optionally substituted aryl groups as also defined above.

The term "arylene" refers to the diradical derived from aryl (including substituted aryl) as defined above and is exemplified by 1,2-phenylene, 1,3-phenylene, 1,4-phenylene, 1,2-naphthylene and the like.

The term "amino" refers to the group —NH$_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic provided that both R's are not hydrogen.

"Amino acid" refers to any of the naturally occurring amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D, L, or DL form. The side chains of naturally occurring amino acids are well known in the art and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), alkaryl (e.g., as in phenylalanine and tryptophan), substituted arylalkyl (e.g., as in tyrosine), and heteroarylalkyl (e.g., as in histidine).

The term "carboxy" refers to —COOH.

The term "C-terminus" as it relates to a glycopeptide is well understood in the art. For example, for a glycopeptide of formula I, the C-terminus is the position substituted by the group $R^3$.

The term "dicarboxy-substituted alkyl" refers to an alkyl group substituted with two carboxy groups. This term includes, by way of example, —CH$_2$(COOH)CH$_2$COOH and —CH$_2$(COOH)CH$_2$CH$_2$COOH.

The term "carboxyalkyl" or "alkoxycarbonyl" refers to the groups "—C(O)O-alkyl", "—C(O)O-substituted alkyl", "—C(O)O-cycloalkyl", "—C(O)O-substituted cycloalkyl", "—C(O)O-alkenyl", "—C(O)O-substituted alkenyl", "—C(O)O-alkynyl" and "—C(O)O-substituted alkynyl" where alkyl, substituted alkyl, cycloalkyl, substituted cycloalkyl, alkenyl, substituted alkenyl, alkynyl and substituted alkynyl are as defined herein.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "cycloalkenyl" refers to cyclic alkenyl groups of from 4 to 20 carbon atoms having a single cyclic ring and at least one point of internal unsaturation. Examples of suitable cycloalkenyl groups include, for instance, cyclobut-2-enyl, cyclopent-3-enyl, cyclooct-3-enyl and the like.

The term "substituted cycloalkenyl" refers to cycloalkenyl groups having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "halo" or "halogen" refers to fluoro, chloro, bromo and iodo.

"Haloalkyl" refers to alkyl as defined herein substituted by 1–4 halo groups as defined herein, which may be the same or different. Representative haloalkyl groups include, by way of example, trifluoromethyl, 3-fluorododecyl, 12,12, 12-trifluorododecyl, 2-bromooctyl, 3-bromo-6-chloroheptyl, and the like.

The term "heteroaryl" refers to an aromatic group of from 1 to 15 carbon atoms and 1 to 4 heteroatoms selected from oxygen, nitrogen and sulfur within at least one ring (if there is more than one ring).

Unless otherwise constrained by the definition for the heteroaryl substituent, such heteroaryl groups can be optionally substituted with 1 to 5 substituents, preferably 1 to 3 substituents, selected from the group consisting of acyloxy, hydroxy, thiol, acyl, alkyl, alkoxy, alkenyl, alkynyl, cycloalkyl, cycloalkenyl, substituted alkyl, substituted alkoxy, -substituted alkenyl, substituted alkynyl, substituted cycloalkyl, substituted cycloalkenyl, amino, substituted amino, aminoacyl, acylamino, alkaryl, aryl, aryloxy, azido, carboxy, carboxyalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl. Preferred aryl substituents include alkyl, alkoxy, halo, cyano, nitro, trihalomethyl, and thioalkoxy. Such heteroaryl groups can have a single ring (e.g., pyridyl or furyl) or multiple condensed rings (e.g., indolizinyl or benzothienyl). Preferred heteroaryls include pyridyl, pyrrolyl and furyl.

"Heteroarylalkyl" refers to (heteroaryl)alkyl- where heteroaryl and alkyl are as defined herein. Representative examples include 2-pyridylmethyl and the like.

The term "heteroaryloxy" refers to the group heteroaryl-O—.

The term "heteroarylene" refers to the diradical group derived from heteroaryl (including substituted heteroaryl), as defined above, and is exemplified by the groups 2,6-pyridylene, 2,4-pyridiylene, 1,2-quinolinylene, 1,8-quinolinylene, 1,4-benzofuranylene, 2,5-pyridnylene, 2,5-indolenyl and the like.

The term "heterocycle" or "heterocyclic" refers to a monoradical saturated or unsaturated group having a single ring or multiple condensed rings, from 1 to 40 carbon atoms and from 1 to 10 hetero atoms, preferably 1 to 4 heteroatoms, selected from nitrogen, sulfur, phosphorus, and/or oxygen within the ring.

Unless otherwise constrained by the definition for the heterocyclic substituent, such heterocyclic groups can be optionally substituted with 1 to 5, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, oxo (=O), and —SO$_2$-heteroaryl. Such heterocyclic groups can have a single ring or multiple condensed rings. Preferred heterocyclics include morpholino, piperidinyl, and the like.

Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles.

Another class of heterocyclics is known as "crown compounds" which refers to a specific class of heterocyclic compounds having one or more repeating units of the formula [—(CH$_2$—)$_a$A-] where a is equal to or greater than 2, and A at each separate occurrence can be O, N, S or P. Examples of crown compounds include, by way of example only, [—(CH$_2$)$_3$—NH—]$_3$, [—((CH$_2$)$_2$—O)$_4$—((CH$_2$)$_2$—NH)$_2$] and the like. Typically such crown compounds can have from 4 to 10 heteroatoms and 8 to 40 carbon atoms.

The term "heterocyclooxy" refers to the group heterocyclic-O—.

The term "thioheterocyclooxy" refers to the group heterocyclic-S—.

The term "oxyacylamino" or "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

The term "phosphono" refers to —PO$_3$H$_2$.

The term "prodrug" is well understood in the art and includes compounds that are converted to pharmaceutically active compounds of the invention in a mammalian system. For example, see *Remington's Pharmaceutical Sciences,* 1980, vol. 16, Mack Publishing Company, Easton, Pa., 61 and 424.

The term "saccharide group" refers to an oxidized, reduced or substituted saccharide monoradical covalently attached to the glycopeptide or other compound via any atom of the saccharide moiety, preferably via the aglycone carbon atom. The term includes amino-containing saccharide groups. Representative saccharides include, by way of illustration, hexoses such as D-glucose, D-mannose, D-xylose, D-galactose, vancosamine, 3-desmethyl-vancosamine, 3-epi-vancosamine, 4-epi-vancosamine, acosamine, actinosamine, daunosamine, 3-epi-daunosamine, ristosamine, D-glucamine, N-methyl-D-glucamine, D-glucuronic acid, N-acetyl-D-glucosamine, N-acetyl-D-galactosamine, sialyic acid, iduronic acid, L-fucose, and the like; pentoses such as D-ribose or D-arabinose; ketoses such as D-ribulose or D-fructose; disaccharides such as 2-O-(α-L-vancosaminyl)-β-D-glucopyranose, 2-O-(3-desmethyl-α-L-vancosaminyl)-β-D-glucopyranose, sucrose, lactose, or maltose; derivatives such as acetals, amines, acylated, sulfated and phosphorylated sugars; oligosaccharides having from 2 to 10 saccharide units. For the purposes of this definition, these saccharides are referenced using conventional three letter nomenclature and the saccharides can be either in their open or preferably in their pyranose form.

The term "amino-containing saccharide group" or "amino saccharide" refers to a saccharide group having an amino substituent. Representative amino-containing saccharides include L-vancosamine, 3-desmethyl-vancosamine, 3-epi-vancosamine, 4-epi-vancosamine, acosamine, actinosamine, daunosamine, 3-epi-daunosamine, ristosamine, N-methyl-D-glucamine and the like.

The term "spiro-attached cycloalkyl group" refers to a cycloalkyl group attached to another ring via one carbon atom common to both rings.

The term "stereoisomer" as it relates to a given compound is well understood in the art, and refers another compound having the same molecular formula, wherein the atoms making up the other compound differ in the way they are oriented in space, but wherein the atoms in the other compound are like the atoms in the given compound with respect to which atoms are joined to which other atoms (e.g. an enantiomer, a diastereomer, or a geometric isomer). See for example, *Morrison and Boyde Organic Chemistry*, 1983, *4th ed*, Allyn and Bacon, Inc., Boston, Mass., page 123.

The term "sulfonamide" refers to a group of the formula —$SO_2NRR$, where each R is independently hydrogen, alkyl, substituted alkyl, aryl, heteroaryl, or heterocyclic wherein alkyl, substituted alkyl, aryl, heteroaryl and heterocyclic are as defined herein.

The term "thiol" refers to the group —SH.

The term "thioalkoxy" refers to the group —S-alkyl.

The term "substituted thioalkoxy" refers to the group —S-substituted alkyl.

The term "thioaryloxy" refers to the group aryl-S— wherein the aryl group is as defined above including optionally substituted aryl groups also defined above.

The term "thioheteroaryloxy" refers to the group heteroaryl-S— wherein the heteroaryl group is as defined above including optionally substituted aryl groups as also defined above.

The term "thioether derivatives" when used to refer to the glycopeptide compounds of this invention includes thioethers (—S—), sulfoxides (—SO—) and sulfones (—$SO_2$—).

As to any of the above groups which contain one or more substituents, it is understood, of course, that such groups do not contain any substitution or substitution patterns which are sterically impractical and/or synthetically non-feasible. In addition, the compounds of this invention include all stereochemical isomers arising from the substitution of these compounds.

"Cyclodextrin" refers to cyclic molecules containing six or more α-D-glucopyranose units linked at the 1,4 positions by α linkages as in amylose. β-Cyclodextrin or cycloheptaamylose contains seven α-D-glucopyranose units. As used herein, the term "cyclodextrin" also includes cyclodextrin derivatives such as hydroxypropyl and sulfobutyl ether cyclodextrins, and others. Such derivatives are described for example, in U.S. Pat. Nos. 4,727,064 and 5,376,645. Additionally, hydroxypropyl-β-cyclodextrin and sulfobutyl-β-cyclodextrin are commercially available. One preferred cyclodextrin is hydroxypropyl β-cyclodextrin having a degree of substitution of from about 4.1–5.1 as measured by FTIR. Such a cyclodextrin is available from Cerestar (Hammond, Ind., USA) under the name Cavitron™ 82003.

The term "aqueous cyclodextrin carrier" refers to an aqueous cyclodextrin solution comprising a cyclodextrin and water.

"Glycopeptide" refers to oligopeptide (e.g. heptapeptide) antibiotics, characterized by a multi-ring peptide core optionally substituted with saccharide groups, such as vancomycin. Examples of glycopeptides included in this definition may be found in "Glycopeptides Classification, Occurrence, and Discovery", by Raymond C. Rao and Louise W. Crandall, ("Drugs and the Pharmaceutical Sciences" Volume 63, edited by Ramakrishnan Nagarajan, published by Marcal Dekker, Inc.). Additional examples of glycopeptides are disclosed in U.S. Pat. Nos. 4,639,433; 4,643,987; 4,497,802; 4,698,327; 5,591,714; 5,840,684; and 5,843,889; in EP 0 802 199; EP 0 801 075; EP 0 667 353; WO 97/28812; WO 97/38702; WO 98/52589; WO 98/52592; and in *J. Amer. Chem. Soc.*, 1996, 118, 13107–13108; *J. Amer. Chem. Soc.*, 1997, 119, 12041–12047; and *J. Amer. Chem. Soc.*, 1994, 116, 4573–4590. Representative glycopeptides include those identified as A477, A35512, A40926, A41030, A42867, A47934, A80407, A82846, A83850, A84575, AB-65, Actaplanin, Actinoidin, Ardacin, Avoparcin, Azureomycin, Balhimycin, Chloroorientiein, Chloropolysporin, Decaplanin, N-demethylvancomycin, Eremomycin, Galacardin, Helvecardin, Izupeptin, Kibdelin, LL-AM374, Mannopeptin, MM45289, MM47756, MM47761, MM49721, MM47766, MM55260, MM55266, MM55270, MM56597, MM56598, OA-7653, Orenticin, Parvodicin, Ristocetin, Ristomycin, Synmonicin, Teicoplanin, UK-68597, UK-69542, UK-72051, Vancomycin, and the like. The term "glycopeptide" or "glycopeptide antibiotic" as used herein is also intended to include the general class of glycopeptides disclosed above on which the sugar moiety is absent, i.e. the aglycone series of glycopeptides. For example, removal of the disaccharide moiety appended to the phenol on vancomycin by mild hydrolysis gives vancomycin aglycone. Also included within the scope of the term "glycopeptide antibiotics" are synthetic derivatives of the general class of glycopeptides disclosed above, included alkylated and acylated derivatives. Additionally, within the scope of this term are glycopeptides that have been further appended with additional saccharide residues, especially aminoglycosides, in a manner similar to vancosamine.

The term "lipidated glycopeptide" refers specifically to those glycopeptide antibiotics which have been synthetically modified to contain a lipid substituent. As used herein, the term "lipid substituent" refers to any substituent contains 5 or more carbon atoms, preferably, 10 to 40 carbon atoms. The lipid substituent may optionally contain from 1 to 6 heteroatoms selected from halo, oxygen, nitrogen, sulfur and phosphorous. Lipidated glycopeptide antibiotics are well-known in the art. See, for example, in U.S. Pat. Nos. 5,840,684, 5,843,889, 5,916,873, 5,919,756, 5,952,310, 5,977,062, 5,977,063, and EP 667, 353, WO 98/52589, WO 99/56760, WO 00/04044, WO 00/39156, the disclosures of which are incorporated herein by reference in their entirety.

"Vancomycin" refers to a glycopeptide antibiotic having the formula:

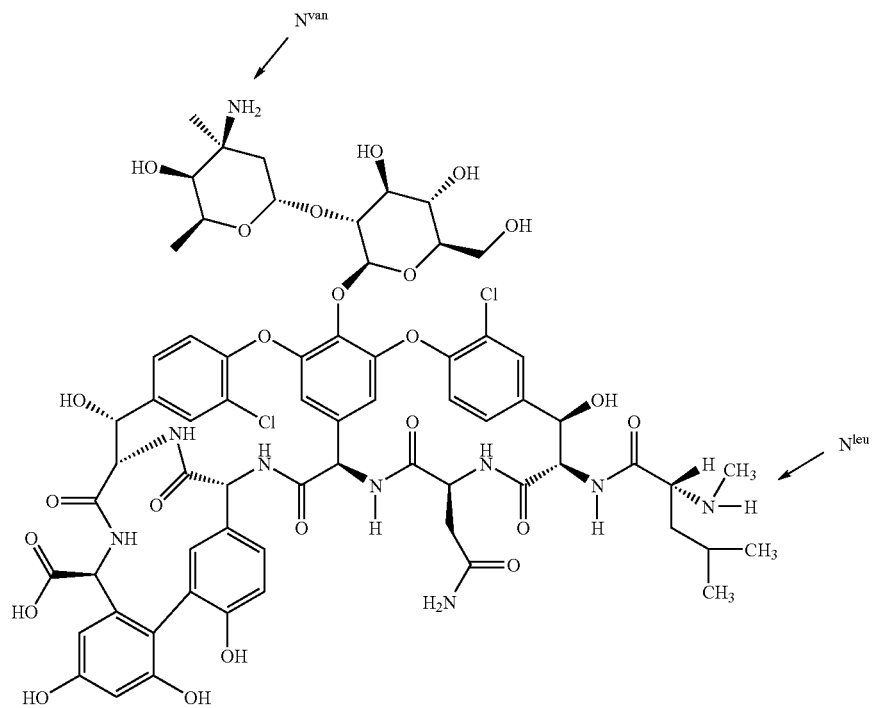

When describing vancomycin derivatives, the term "N$^{van}$-" indicates that a substituent is covalently attached to the amino group of the vacosamine moiety of vacomycin. Similarly, the term "N$^{leu}$-" indicates that a substituent is covalently attached to the amino group of the leucine moiety of vancomycin.

"Optional" or "optionally" means that the subsequently described event or circumstance may or may not occur, and that the description includes instances where said event or circumstance occurs and instances in which it does not. For example, "optionally substituted" means that a group may or may not be substituted with the described substituent.

As used herein, the terms "inert organic solvent" or "inert solvent" or "inert diluent" mean a solvent or diluent which is essentially inert under the conditions of the reaction in which it is employed as a solvent or diluent. Representative examples of materials which may be used as inert solvents or diluents include, by way of illustration, benzene, toluene, acetonitrile, tetrahydrofuran ("THF"), dimethylformamide ("DMF"), chloroform ("CHCl$_3$"), methylene chloride (or dichloromethane or "CH$_2$Cl$_2$"), diethyl ether, ethyl acetate, acetone, methylethyl ketone, methanol, ethanol, propanol, isopropanol, tert-butanol, dioxane, pyridine, and the like. Unless specified to the contrary, the solvents used in the reactions of the present invention are inert solvents.

The term "nitrogen-linked" or "N-linked" means a group or substituent is attached to the remainder of a compound (e.g. a compound of formula I) through a bond to a nitrogen of the group or substituent. The term "oxygen-linked" means a group or substituent is attached to the remainder of a compound (e.g. a compound of formula I) through a bond to an oxygen of the group or substituent. The term "sulfur-linked" means a group or substituent is attached to the remainder of a compound (e.g. a compound of formula I) through a bond to a sulfur of the group or substituent.

"Pharmaceutically acceptable salt" means those salts which retain the biological effectiveness and properties of the parent compounds and which are not biologically or otherwise harmful as the dosage administered. The compounds of this invention are capable of forming both acid and base salts by virtue of the presence of amino and carboxy groups, respectively.

Pharmaceutically acceptable base addition salts may be prepared from inorganic and organic bases. Salts derived from inorganic bases include, but are not limited to, the sodium, potassium, lithium, ammonium, calcium, and magnesium salts. Salts derived from organic bases include, but are not limited to, salts of primary, secondary and tertiary amines, substituted amines including naturally-occurring substituted amines, and cyclic amines, including isopropylamine, trimethyl amine, diethylamine, triethylamine, tripropylamine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, and N-ethylpiperidine. It should also be understood that other carboxylic acid derivatives would be useful in the practice of this invention, for example carboxylic acid amides, including carboxamides, lower alkyl carboxamides, di(lower alkyl) carboxamides, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

The compounds of this invention typically contain one or more chiral centers. Accordingly, this invention is intended to include racemic mixtures, diasteromers, enantiomers and mixture enriched in one or more steroisomer. The scope of the invention as described and claimed encompasses the racemic forms of the compounds as well as the individual enantiomers and non-racemic mixtures thereof.

The term "treatment" as used herein includes any treatment of a condition or disease in an animal, particularly a mammal, more particularly a human, and includes:

(i) preventing the disease or condition from occurring in a subject which may be predisposed to the disease but has not yet been diagnosed as having it;

(ii) inhibiting the disease or condition, i.e. arresting its development; relieving the disease or condition, i.e. causing regression of the condition; or relieving the conditions caused by the disease, i.e. symptoms of the disease.

The term "disease state which is alleviated by treatment with a broad spectrum antibacterial" or "bacterial disease" as used herein is intended to cover all disease states which are generally acknowledged in the art to be usefully treated with a broad spectrum antibacterial in general, and those disease states which have been found to be usefully treated by the specific antibacterials of this invention. Such disease states include, but are not limited to, treatment of a mammal afflicted with pathogenic bacteria, in particular staphylococci (methicillin sensitive and resistant), streptococci (penicillin sensitive and resistant), enterococci (vancomycin sensitive and resistant), and Clostridium difficile The term "therapeutically effective amount" refers to that amount which is sufficient to effect treatment, as defined herein, when administered to a mammal in need of such treatment. The therapeutically effective amount will vary depending on the subject and disease state being treated, the severity of the affliction and the manner of administration, and may be determined routinely by one of ordinary skill in the art.

The term "protecting group" or "blocking group" refers to any group which, when bound to one or more hydroxyl, thiol, amino, carboxy or other groups of the compounds, prevents undesired reactions from occurring at these groups and which protecting group can be removed by conventional chemical or enzymatic steps to reestablish the hydroxyl, thio, amino, carboxy or other group. The particular removable blocking group employed is not critical and preferred removable hydroxyl blocking groups include conventional substituents such as allyl, benzyl, acetyl, chloroacetyl, thiobenzyl, benzylidine, phenacyl, t-butyl-diphenylsilyl and any other group that can be introduced chemically onto a hydroxyl functionality and later selectively removed either by chemical or enzymatic methods in mild conditions compatible with the nature of the product. Protecting groups are disclosed in more detail in T. W. Greene and P. G. M. Wuts, "Protective Groups in Organic Synthesis" 3$^{rd}$ Ed., 1999, John Wiley and Sons, N.Y.

Preferred removable amino blocking groups include conventional substituents such as t-butyoxycarbonyl (t-BOC), benzyloxycarbonyl (CBZ), fluorenylmethoxycarbonyl (FMOC), allyloxycarbonyl (ALOC) and the like, which can be removed by conventional conditions compatible with the nature of the product.

Preferred carboxy protecting groups include esters such as methyl, ethyl, propyl, t-butyl etc. which can be removed by mild conditions compatible with the nature of the product.

General Synthetic Procedures

The glycopeptide antibiotics employed in this invention are commercially available or can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and G. M. Wuts, *Protecting Groups in Organic Synthesis*, Third Edition, Wiley, New York, 1999, and references cited therein.

In the following reaction schemes, the glycopeptide compounds are depicted in a simplified form as a box "G" that shows the carboxy terminus labeled [C], the vancosamine amino terminus labeled [V], the "non-saccharide" amino terminus (leucine amine moiety) labeled [N], and optionally, the resorcinol moiety labeled [R] as follows:

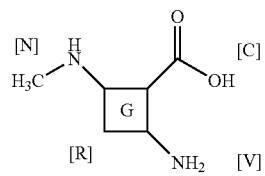

By way of illustration, a lipidated glycopeptide compound useful in the present invention can be prepared by reductive alkylated as shown in the following reaction:

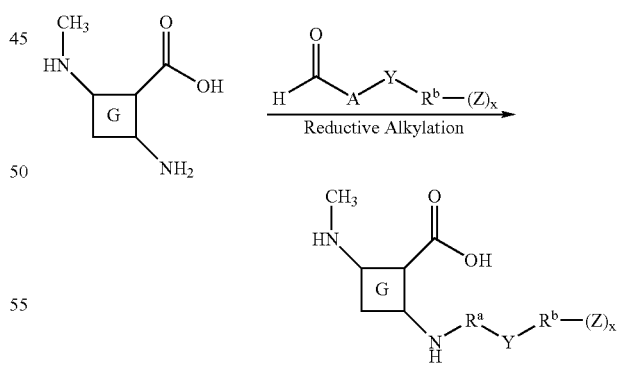

where A represents $R^a$ minus one carbon atom and $R^a$, $R^b$, Y, Z and x are as defined herein. This reaction is typically conducted by first contacting one equivalent of the glycopeptide, i.e., vancomycin, with an excess, preferably from 1.1 to 1.3 equivalents, of the desired aldehyde in the presence of an excess, preferably about 2.0 equivalents, of a tertiary amine, such as diisopropylethylamine (DIPEA) and the like. This reaction is typically conducted in an inert diluent, such as DMF or acetonitrile/water, at ambient temperature for about 0.25 to 2 hours until formation of the corresponding imine and/or hemiaminal is substantially complete. The resulting imine and/or hemiaminal is typically not isolated, but is reacted in situ with a metal hydride reducing agent, such as sodium cyanoborohydride and the like, to afford the corresponding amine. This reaction is preferably conducted by contacting the imine and/or hemiaminal with an excess, preferably about 3 equivalents, of trifluoroacetic acid, followed by about 1 to 1.2 equivalents of the reducing agent at ambient temperature in methanol or acetonitrile/water. The resulting alkylated product is readily purified by conventional procedures, such as precipitation and/or reverse-phase high-performance liquid chromatography (HPLC). Surprisingly, by forming the imine and/or hemiaminal in the presence of a trialkyl amine, and then acidifying with trifluoroacetic acid before contact with the reducing agent, the selectivity for the reductive alkylation reaction is greatly improved, i.e., reductive alkylation at the amino group of the saccharide (e.g., vancosamine) is favored over reductive alkylation at the N-terminus (e.g., the leucinyl group) by at least 10:1, more preferably 20:1.

The reductive alkylation process is typically carried out in the presence of a suitable solvent or combination of solvents, such as, for example, a halogenated hydrocarbon (e.g. methylene chloride), a linear or branched ether (e.g. diethyl ether, tetrahydrofuran), an aromatic hydrocarbon (e.g. benzene or toluene), an alcohol (methanol, ethanol, or isopropanol), dimethylsulfoxide (DMSO), N,N-dimethylformamide, acetonitrile, water, 1,3-dimethyl-3,4,5,6-tetrahydro-2 (1H)-pyrimidone, tetramethyl urea, N,N-dimethylacetamide, diethylformamide (DMF), 1-methyl-2-pyrrolidinone, tetramethylenesulfoxide, glycerol, ethyl acetate, isopropyl acetate, N,N-dimethylpropylene urea (DMPU) or dioxane. Preferably the alkylation is carried out in acetonitrile/water, or DMF/methanol.

Preferably the reduction (i.e. treatment with the reducing agent) is carried out in the presence of a protic solvent, such as, for example, an alcohol (e.g. methanol, ethanol, propanol, isopropanol, or butanol), water, or the like.

The reductive alkylation process of the invention can be carried out at any suitable temperature from the freezing point to the reflux temperature of the reaction mixture. Preferably the reaction is carried out at a temperature in the range of about 0° C. to about 100° C. More preferably at a temperature in a range of about 0° C. to about 50° C., or in a range of about 20° C. to about 30° C.

Any suitable base can be employed in the reductive alkylation process of the invention. Suitable bases include tertiary amines (e.g. diisopropylethylamine, N-methylmorpholine or triethylamine) and the like.

Any suitable acid can be used to acidify the reaction mixture. Suitable acids include carboxylic acids (e.g. acetic acid, trichloroacetic acid, citric acid, formic acid, or trifluoroacetic acid), mineral acids (e.g. hydrochloric acid, sulfuric acid, or phosphoric acid), and the like. A preferred acid is trifluoroacetic acid.

Suitable reducing agents for carrying out reductive alkylation process of the invention are known in the art. Any suitable reducing agent can be employed in the methods of the invention, provided it is compatible with the functionality present in the glycopeptide. For example, suitable reducing agents include sodium cyanoborohydride, triacetoxyborohydride, pyridine/borane, sodium borohydride, and zinc borohydride. The reduction can also be carried out in the presence of a transition metal catalyst (e.g. palladium or platinum) in the presence of a hydrogen source (e.g. hydrogen gas or cycloheadiene). See for example, *Advanced Organic Chemistry*, Fourth Edition, John Wiley & Sons, New York (1992), 899–900.

Any glycopeptide having an amino group may be employed in these reductive alkylation reactions. Such glycopeptides are well-known in the art and are either commercially available or may be isolated using conventional procedures. Suitable glycopeptides are disclosed, by way of example, in U.S. Pat. Nos. 3,067,099; 3,338,786; 3,803,306; 3,928,571; 3,952,095; 4,029,769; 4,051,237; 4,064,233; 4,122,168; 4,239,751; 4,303,646; 4,322,343; 4,378,348; 4,497,802; 4,504,467; 4,542,018; 4,547,488; 4,548,925; 4,548,974; 4,552,701; 4,558,008; 4,639,433; 4,643,987; 4,661,470; 4,694,069; 4,698,327; 4,782,042; 4,914,187; 4,935,238; 4,946,941; 4,994,555; 4,996,148; 5,187,082; 5,192,742; 5,312,738; 5,451,570; 5,591,714; 5,721,208; 5,750,509; 5,840,684; and 5,843,889. Preferably, the glycopeptide employed in the above reaction is vancomycin.

The aldehydes and ketones employed in the above reactive alkylation reactions are also well-known in the art and are either commercially available or can be prepared by conventional procedures using commercially available starting materials and conventional reagents (for example see March, *Advanced Organic Chemistry*, Fourth Edition, John Wiley & Sons, New York (1992), and references cited therein). Aldehydes and ketones other than those shown above may be employed in this alkylation reaction, including by way of example, aldehydes of the formula HC(O)—$R^f$, where $R^f$ is as defined herein.

If desired, aminoalkyl sidechain can be introduced at the resorcinol moiety of a glycopeptide, such as vancomycin, via a Mannich reaction. In this reaction, an amine of formula NHRR' (wherein one or both of R and R' is a alkyl or substituted alkyl group or a group that comprises one or more phosphono groups), and an aldehyde ($CH_2O$), such as formalin (a source of formaldehyde), are reacted with the glycopeptide under basic conditions to give the glycopeptide derivative, as shown below (in this scheme, the resorcinol moiety is shown for clarity).

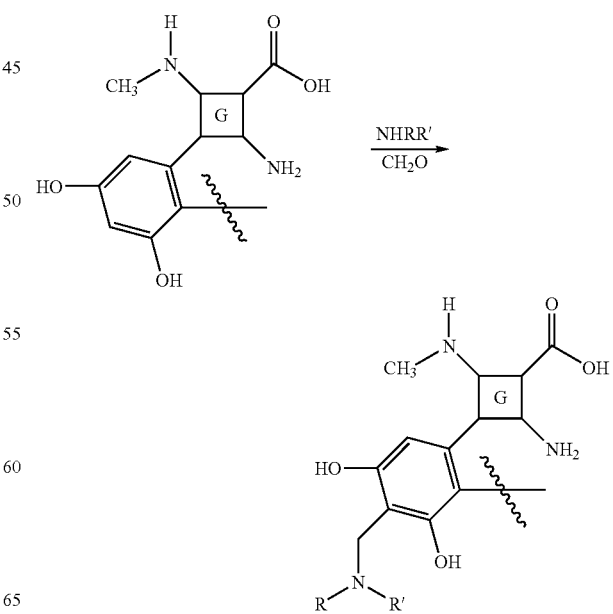

When employed, the phosphono substituted compounds (e.g. the phosphono substituted amines, alcohols, or thiols) are either commercially available or can be prepared by conventional procedures using commercially available starting materials and reagents. See for example, *Advanced Organic Chemistry*, Jerry March, 4th ed, 1992, John Wiley and Sons, New York, page 959; and Frank R. Hartley (ed.) *The Chemistry of Organophosphorous Compounds*, vol. 1–4, John Wiley and Sons, New York (1996). Aminomethylphosphonic acid is commercially available from Aldrich Chemical Company, Milwaukee, Wis.

Additional details and other methods for preparing the compounds of this invention are described in the Examples below.

Pharmaceutical Compositions

The pharmaceutical compositions of this invention comprise a glycopeptide antibiotic and a cyclodextrin compound. Preferably, the pharmaceutical compositions of this invention are formulated for parenteral administration for the therapeutic or prophylactic treatment of bacterial diseases.

By way of illustration, the glycopeptide antibiotic, preferably in the form a pharmaceutically acceptable salt, can be admixed with an aqueous cyclodextrin solution to form a composition of this invention. Such pharmaceutical compositions will typically contain from about 1 to about 40 weight percent of the cyclodextrin and a therapeutically effective amount of the glycopeptide antibiotic.

Optionally, the pharmaceutical composition may contain other pharmaceutically acceptable components, such a buffers, surfactants, antioxidants, viscosity modifying agents, preservatives and the like. Each of these components is well-known in the art. See, for example, U.S. Pat. No. 5,985,310. Other components suitable for use in the formulations of the present invention can be found in *Remington's Pharmaceutical Sciences*, Mace Publishing Company, Philadelphia, Pa., 17th ed. (1985). In a preferred embodiment, the aqueous cyclodextrin solution further comprises dextrose, preferably, 5% dextrose.

The glycopeptide antibiotics used in this invention are effective over a wide dosage range and are typically administered in a therapeutically effective amount. It, will be understood, however, that the amount of the compound actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

Suitable doses are in the general range of from 0.01–100 mg/kg/day, preferably 0.1–50 mg/kg/day. For an average 70 kg human, this would amount to 0.7 mg to 7 g per day, or preferably 7 mg to 3.5 g per day. A more preferred dose for a human is about 500 mg to about 2 g per day.

The following formulation examples illustrate representative pharmaceutical compositions of the invention.

FORMULATION EXAMPLE A

An injectable preparation is prepared having the following composition:

| Ingredients | |
| --- | --- |
| Glycopeptide Antibiotic | 0.1–5.0 g |
| Hydroxypropyl-β-cyclodextrin | 1–25 g |
| 5% Aqueous Dextrose Solution (sterile) | q.s. to 100 mL |

The above ingredients are blended and the pH is adjusted to 3.5 ± 0.5 using 0.5 N HCl or 0.5 N NaOH.

FORMULATION EXAMPLE B

This example illustrates the preparation of a representative pharmaceutical composition containing a compound of this invention.

A frozen solution suitable for injection is prepared having the following composition:

| Frozen Solution | |
| --- | --- |
| Active Compound | 250 mg to 1000 mg |
| Hydroxypropyl-β-cyclodextrin | 250 mg to 10 g |
| Excipients - e.g., dextrose | 0–50 g |
| Water for Injection | 10–100 mL |

The weight ratio of hydroxypropyl-β-cyclodextrin to the active compound will typically be from about 1:1 to about 10:1.

Representative Procedure: Hydroxypropyl-β-cyclodextrin and excipients, if any, are dissolved in about 80% of the water for injection and the active compound is added and dissolved. The pH is adjusted with 1 M sodium hydroxide to 4.7±0.3 and the volume is then adjusted to 95% of the final volume with water for injection. The pH is checked and adjusted, if necessary, and the volume is adjusted to the final volume with water for injection. The formulation is then sterile filtered through a 0.22 micron filter and placed into a sterile vial under aseptic conditions. The vial is capped, labeled and stored frozen.

FORMULATION EXAMPLE C

This example illustrates the preparation of a representative pharmaceutical composition containing a compound of this invention.

A lyophilized powder useful for preparing an injectable solution is prepared having the following composition:

| Lyophilized Powder | |
| --- | --- |
| Active Compound | 250 mg to 1000 mg |
| Hydroxypropyl-β-cyclodextrin | 250 mg to 10 g |
| Excipients - e.g., mannitol, sucrose and/or lactose | 0–50 g |
| Buffer agent - e.g., citrate | 0–500 mg |

The weight ratio of hydroxypropyl-β-cyclodextrin to the active compound will typically be from about 1:1 to about 10:1.

Representative Procedure: Hydroxypropyl-β-cyclodextrin and excipients and/or buffering agents, if any, are dissolved in about 60% of the water for injection. The active compound is added and dissolved and the pH is adjusted with 1 M sodium hydroxide to 4.0–5.0 and the volume is adjusted to 95% of the final volume with water for injection. The pH is checked and adjusted, if necessary, and the volume is adjusted to the final volume with water for injection. The formulation is then sterile filtered through a 0.22 micron filter and placed into a sterile vial under aseptic conditions. The formulation is then freeze-dried using an appropriate lyophilization cycle. The vial is capped (optionally under partial vacuum or dry nitrogen), labeled and stored at room temperature or under refrigeration.

FORMULATION EXAMPLE D

This example illustrates the preparation of a representative pharmaceutical composition containing a compound of this invention.

A sterile powder useful for preparing an injectable solution is prepared having the following composition:

| Sterile Powder | |
|---|---|
| Active Compound | 250 mg to 1000 mg |
| Hydroxypropyl-β-cyclodextrin | 250 mg to 10 g$^1$ |
| Excipients | optional |

The weight ratio of hydroxypropyl-β-cyclodextrin to the active will typically be from about 1:1 to about 10:1.

Representative Procedure: Hydroxypropyl-β-cyclodextrin and the active compound (and any excipients) are dispersed into an appropriate sterile container and the container is sealed (optionally under partial vacuum or dry nitrogen), labeled and stored at room temperature or under refrigeration.

Administration of Representative Formulations C and D to a Patient

The pharmaceutical formulations described in formulation examples H and I above can be administered intravenously to a patient by the appropriate medical personnel to treat or prevent gram-positive infections. For administration, the above formulations can be reconstituted and/or diluted with a diluent, such as 5% dextrose or sterile saline, as follows:

Representative Procedure: The lyophilized powder of formulation example C (e.g., containing 1000 mg of active compound) is reconstituted with 20 mL of sterile water and the resulting solution is further diluted with 80 mL of sterile saline in a 100 mL infusion bag. The diluted solution is then administered to the patient intravenously over 30 to 120 minutes.

Utility

The pharmaceutical compositions of this invention are useful in medical treatments and exhibit biological activity, including antibacterial activity, which can be demonstrated in using the tests described herein. Such tests are well known to those skilled in the art, and are referenced and described in Lorian "Antibiotics in Laboratory Medicine", Fourth Edition, Williams and Wilkins (1991).

Accordingly, this invention provides methods for treating bacterial or infectious diseases, especially those caused by Gram-positive microorganisms, in animals. Depending on the glycopeptide antibiotic, the compositions of this invention are particularly useful in treating infections caused by methicillin-resistant staphylococci.

The animal treated with the pharmaceutical compositions of this invention may be either susceptible to, or infected with, the microorganism. The method of treatment typically comprises administering to the animal a pharmaceutical composition comprising a therapeutically effective amount of the glycopeptide antibiotic compound.

In practicing this method, the pharmaceutical composition can be administered in a single daily dose or in multiple doses per day. The treatment regimen may require administration over extended periods of time, for example, for several days or for from one to six weeks. The amount per administered dose or the total amount administered will depend on such factors as the nature and severity of the infection, the age and general health of the patient, the tolerance of the patient to the antibiotic and the microorganism or microorganisms in the infection.

Among other properties, when administered to a mammal, the pharmaceutical compositions of this invention have been found to exhibit one or more of the following properties (a) reduced tissue accumulation of the glycopeptide antibiotic, (b) reduced nephrotoxicity, (c) reduced histamine release (Red Man Syndrome) and (d) reduced vascular irritation, compared to a pharmaceutical composition which does not contain the cyclodextrin. Additionally, the cyclodextrin has been found to increase the water solubility of certain glycopeptide antibiotics, such as lipidated glycopeptide antibiotics.

The following synthetic and biological examples are offered to illustrate this invention and are not to be construed in any way as limiting the scope of this invention.

EXAMPLES

In the examples below, the following abbreviations have the following meanings. Any abbreviations not defined have their generally accepted meaning. Unless otherwise stated, all temperatures are in degrees Celsius.

ACN=acetonitrile
BOC, Boc=tert-butoxycarbonyl
DIBAL-H=diisobutylaluminum hydride
DIPEA=diisopropylethylamine
DMF=N,N-dimethylformamide
DMSO=dimethyl sulfoxide
eq.=equivalent
EtOAc=ethyl acetate
Fmoc=9-fluorenylmethoxycarbonyl
HOBT=1-hydroxybenzotriazole hydrate
Me=methyl
PyBOP=benzotriazol-1-yloxytris(pyrrolidino)phosphonium hexafluorophosphate
TEMPO=2,2,6,6tetramethyl-piperidinyloxy, free radical
TFA=trifluoroacetic acid
THF=tetrahydrofuran
TLC, tlc=thin layer chromatography In the following examples, vancomycin hydrochloride semi-hydrate was purchased from Alpharma, Inc. Fort Lee, N.J. 07024 (Alpharma AS, Oslo Norway). Other reagents and reactants are available from Aldrich Chemical Co., Milwaukee, Wis. 53201.

General Procedure A

Reductive Alkylation of Vancomycin

To a mixture of vancomycin (1 eq.) and the desired aldehyde (1.3 eq.) in DMF was added DIPEA (2 eq.). The reaction was stirred at ambient temperature for 1–2 hours and monitored by reverse-phase HPLC. Methanol and NaCNBH$_3$ (1 eq.) were added to the solution, followed by TFA (3 eq.). Stirring was continued for an additional hour at ambient temperature. After the reaction was complete, the methanol was removed in vacuo. The residue was precipitated in acetonitrile. Filtration gave the crude product which was then purified by reverse-phase HPLC. If desired, other glycopeptides antibiotics may be used in this procedure.

Example 1

Preparation of Compound A (Formula II Wherein R$^3$ is —OH; R$^5$ N-(phosphonomethyl)aminomethyl; R$^{19}$ is Hydrogen, and R$^{20}$ is —CH$_2$CH$_2$—NH—(CH$_2$)$_9$CH$_3$)

(Aminomethyl)phosphonic acid (3.88 g, 35 mmol) and diisopropylethylamine (6.1 ml, 35 mmol) were combined in water (40 ml) and stirred until homogeneous. Acetonirile (50 ml) and formaldehyde (37% solution in H$_2$O; 0.42 ml, 05.6 mmol) were then added to the reaction mixture. After approximately 15 minutes both N$^{VAN}$-decylaminoethyl vancomycin tristrifluoroacetate (10.0 g, 5.1 mmol) and diisopropylethylamine (6.1 ml, 35 mmol) were added to the reaction mixture. The reaction was stirred at room temperature for approximately 18 hrs, at which time the acetonitrile was removed in vacuo, and the residue was lyophylized. The resulting solid was triturated with water (100 mL), collected by filtration, dried in vacuo and purified by reverse phase preparative HPLC to give the title compound. MS calculated (MH+) 1756.6; found (MH+) 1756.6.

Example 2

Preparation of Pharmaceutical Compositions

Injectable pharmaceutical compositions can be prepared as follows:

|  | Compound A | Hydroxypropyl-β-cyclodextrin | 5% Aqueous Dextrose Solution (sterile) |
| --- | --- | --- | --- |
| 2A | 200 mg | 1 g | q.s. to 100 mL |
| 2B | 200 mg | 5 g | q.s. to 100 mL |
| 2C | 200 mg | 25 g | q.s. to 100 mL |
| 2D | 200 mg | 30 g | q.s. to 100 mL |

The above ingredients were blended and the pH was adjusted to 3.5±0.5 using 0.5 N HCl or 0.5 N NaOH.

Example 3

Preparation of a Glycopeptide that can be Incorporated into a Composition of the Invention (Formula II Wherein R$^3$ is —OH; R$^5$ is H; R$^{19}$ is Hydrogen, and R$^{20}$ is 4-(4-chlorophenyl)benzyl A three liter 3-necked flask was fitted with a condenser, nitrogen inlet and overhead mechanical stirring apparatus. The flask was charged with pulverized A82846B acetate salt (20.0 g, 1.21×10$^{-5}$ mol) and methanol (1000 mL) under a nitrogen atmosphere, 4'-chlorobiphenylcarboxaldehyde (2.88 g, 1.33×10$^{-2}$ mol, 1.1 eq.) was added to this stirred mixture, followed by methanol (500 mL). Finally, sodium cyanoborohydride (0.84 g, 1.33×10$^{-2}$ mol, 1.1 eq.) was added followed by methanol (500 mL). The resulting mixture was heated to reflux (about 65° C.).

After 1 hour at reflux, the reaction mixture attained homogeneity. After 25 hours at reflux, the heat source was removed and the clear reaction mixture was measured with a pH meter (6.97 at 58.0° C.). 1N NaOH (22.8 mL) was added dropwise to adjust the pH to 9.0 (at 54.7° C.). The flask was equipped with a distillation head and the mixture was concentrated under partial vacuum to a weight of 322.3 grams while maintaining the pot temperature between 40°–45° C.

The distillation head was replaced with an addition funnel containing 500 mL of isopropanol (IPA). The IPA was added dropwise to the room temperature solution over 1 hour. After approximately ⅓ of the IPA was added, a granular precipitate formed. The remaining IPA was added at a faster rate after precipitation had commenced. The flask was weighed and found to hold 714.4 grams of the IPA/methanol slurry.

The flask was re-equipped with a still-head and distilled under partial vacuum to remove the remaining methanol. The resulting slurry (377.8 g) was allowed to chill in the freezer overnight. The crude product was filtered through a polypropylene pad and rinsed twice with 25 mL of cold IPA. After pulling dry on the funnel for 5 minutes, the material was placed in the vacuum oven to dry ta 40° C. A light pink solid (22.87 g (theory=22.43 g)) was recovered. HPLC analysis versus a standard indicated 68.0% weight percent of the title compound (4-[4-chlorophenyl]benzyl-A82846B] in the crude solid, which translated into a corrected crude yield of 69.3%.

The products of the reaction were analyzed by reverse-phase HPLC utilizing a Zorbax SB-C$_{18}$ column with ultraviolet light (UV; 230 nm) detection. A 20 minute gradient solvent system consisting of 95% aqueous buffer/5% CH$_3$CN at time=0 minutes to 40% aqueous buffer/60% CH$_3$CN at time=30 minutes was used, where the aqueous buffer was TEAP (5 ml CH$_3$CN, 3 ml phosphoric acid in 1000 ml water).

The intermediate A82846B acetate salt can be prepared as described in U.S. Pat. No. 5,840,684.

Example 4

Determination of Antibacterial Activity

A. In Vitro Determination of Antibacterial Activity
1. Determination of Minimal Inhibitory Concentrations (MICs)

This procedure may be used to assess the antibacterial properties of the glycopeptide antibiotic. Bacterial strains were obtained from either American Type Tissue Culture Collection (ATCC), Stanford University Hospital (SU), Kaiser Permanente Regional Laboratory in Berkeley (KPB), Massachusetts General Hospital (MGH), the Centers for Disease Control (CDC), the San Francisco Veterans' Administration Hospital (SFVA) or the University of California San Francisco Hospital (UCSF). Vancomycin resistant enterococci were phenotyped as Van A or Van B based on their sensitivity to teicoplanin. Some vancomycin resistant enterococci that had been genotyped as Van A, Van B, Van C1 or Van C2 were obtained from the Mayo Clinic.

Minimal inhibitory concentrations (MICs) were measured in a microdilution broth procedure under NCCLS guidelines. Routinely, the compounds were serially diluted into Mueller-Hinton broth in 96-well microtiter plates. Overnight cultures of bacterial strains were diluted based on absorbance at 600 nm so that the final concentration in each well was $5\times10^5$ cfu/mL. Plates were returned to a 35° C. incubator. The following day (or 24 hours in the case of Enterococci strains), MICs were determined by visual inspection of the plates. Strains routinely tested in the initial screen included methicillin-sensitive *Staphylococcus aureus* (MSSA), methicillin-resistant *Staphylococcus aureus*, methicillin-sensitive *Staphylococcus epidermidis* (MSSE), methicillin-resistant *Staphylococcus epidermidis* (MRSE), vancomycin sensitive *Enterococcus faecium* (VSE Fm), vancomycin sensitive *Enterococcus faecalis* (VSE Fs), vancomycin resistant *Enterococcus faecium* also resistant to teicoplanin (VRE Fm Van A), vancomycin resistant *Enterococcus faecium* sensitive to teicoplanin (VRE Fm Van B), vancomycin resistant *Enterococcus faecalis* also resistant to teicoplanin (VRE Fs Van A), vancomycin resistant *Enterococcus faecalis* sensitive to teicoplanin (VRE Fs Van B), *enterococcus gallinarium* of the Van A genotype (VRE Gm Van A), *enterococcus gallinarium* of the Van C-1 genotype (VRE Gm Van C-1), *enterococcus casseliflavus* of the Van C-2 genotype (VRE Cs Van C-2), *enterococcus flavescens* of the Van C-2 genotype (VRE Fv Van C-2), and penicillin-sensitive *Streptococcus pneumoniae* (PSSP) and penicillin-resistant *Streptococcus pneumoniae* (PSRP). Because of the inability of PSSP and PSRP to grow well in Mueller-Hinton broth, MICs with those strains were determined using either TSA broth supplemented with defibrinated blood or blood agar plates. Compounds which had significant activity against the strains mentioned above were then tested for MIC values in a larger panel of clinical isolates including the species listed above as well as non-speciated coagulase negative *Staphylococcus* both sensitive and resistant to methicillin (MS-CNS and MR-CNS). In addition, they were tested for MICs against gram negative organisms, such as *Escherichia coli* and *Pseudomonas aeruginosa*.

2. Determination of Kill Time

Experiments to determine the time required to kill the bacteria were conducted as described in Lorian, "Antibiotics in Laboratory Medicine", Fourth Edition, Williams and Wilkins (1991). These experiments were conducted normally with both *staphylococcus* and *enterococcus* strains.

Briefly, several colonies were selected from an agar plate and grown at 35° C. under constant agitation until it achieved a turbidity of approximately 1.5 and $10^8$ CFU/mL. The sample was then diluted to about $6\times10^6$ CFU/mL and incubated at 35° C. under constant agitation was continued. At various times aliquots were removed and five ten-fold serial dilutions were performed. The pour plate method was used to determine the number of colony forming units (CFUs).

In general, glycopeptide antibiotics active in the above tests in vitro tests are suitable for use in the pharmaceutical compositions of this invention.

B. In Vivo Determination of Antibacterial Activity

1. Acute Tolerability Studies in Mice

In these studies, a pharmaceutical composition of this invention was administered either intravenously or subcutaneously and observed for 5–15 minutes. If there were no adverse effects, the dose was increased in a second group of mice. This dose incrementation continued until mortality occurred, or the dose was maximized. Generally, dosing began at 20 mg/kg and increased by 20 mg/kg each time until the maximum tolerated dose (MTD) is achieved.

2. Bioavailability Studies in Mice

Mice were administered a compound of this invention either intravenously or subcutaneously at a therapeutic dose (in general, approximately 50 mg/kg). Groups of animals were placed in metabolic cages so that urine and feces could be collected for analysis. Groups of animals (n=3) were sacrificed at various times (10 min, 1 hour and 4 hours). Blood was collected by cardiac puncture and the following organs were harvested—lung, liver, heart, brain, kidney, and spleen. Tissues were weighed and prepared for HPLC analysis. HPLC analysis on the tissue homogenates and fluids was used to determine the concentration of the test compound or IiI present. Metabolic products were also determined at this juncture.

3. Mouse Septicemia Model

In this model, an appropriately virulent strain of bacteria (most commonly *S. aureus*, or *E. Faecalis* or *E. Faecium*) was administered to mice (N=5 to 10 mice per group) intraperitoneally. The bacteria was combined with hog gastric mucin to enhance virulence. The dose of bacteria (normally $10^5$–$10^7$) was that sufficient to induce mortality in all of the mice over a three day period. One hour after the bacteria was administered, a pharmaceutical composition of this invention was administered in a single dose either IV or subcutaneously. Each dose was administered to groups of 5 to 10 mice, at doses that typically ranged from a maximum of about 20 mg/kg to a minimum of less than 1 mg/kg. A positive control (normally vancomycin with vancomycin sensitive strains) was administered in each experiment. The dose at which approximately 50% of the animals are saved was calculated from the results.

4. Neutropenic Thigh Model

In this model, antibacterial activity of a pharmaceutical composition of this invention was evaluated against an appropriately virulent strain of bacteria (most commonly *S. aureus*, or *E. Faecalis* or *E. Faecium*, sensitive or resistant to vancomycin). Mice were initially rendered neutropenic by administration of cyclophosphamide at 200 mg/kg on day 0 and day 2. On day 4 they were infected in the left anterior thigh by an IM injection of a single dose of bacteria. The mice were then administered the test compound one hour after the bacteria and at various later times (normally 1, 2.5, 4 and 24 hours) the mice were sacrificed (3 per time point) and the thigh excised, homogenized and the number of CFUs (colony forming units) were determined by plating. Blood was also plated to determine the CFUs in the blood.

5. Pharmacokinetic Studies

The rate at which a compound of this invention is removed from the blood can be determined in either rats or mice. In rats, the test animals were cannulated in the jugular vein. The test compound was administered via tail vein injection, and at various time points (normally 5, 15, 30,60 minutes and 2,4,6 and 24 hours) blood was withdrawn from the cannula. In mice, the test compound was also administered via tail vein injection, and at various time points. Blood was normally obtained by cardiac puncture. The concentration of the remaining test compound was determined by HPLC.

In general, the pharmaceutical compositions of this invention were active in the above test in vivo and demonstrated a broad spectrum of activity.

Example 5

Determination of Tissue Accumulation

A. Tissue Distribution Using Radiolabeled Compound

This procedure is used to examine the tissue distribution, excretion and metabolism of a radiolabeled test compound in both male and female rats following intravenous infusion at 10 mg/kg. Male and female Sprague-Dawley rats (n=2 per sex per compound) are dosed with $^3$H-labeled test compound at 10 (400 µCi/kg) and 12.5 mg/kg (100 µCi/kg), respectively, via intravenous infusion (~2 min). The test compound is formulated in 5% hydroxypropyl-β-cyclodextrin as 2.5 mg/mL solution. Urine and feces are cage collected over 24 hours period. At 24 hours after dosing, animals are sacrificed and tissues are removed. Serum, urine and tissues are analyzed for total radioactivity by oxidation followed by liquid scintillation counting. Urine and selected tissues samples are extracted and analyzed by reverse phase HPLC with radioactive flow detector for the presence of potential metabolites.

B. Tissue Accumulation Following Single Dose

This procedure is used to evaluate tissue distribution of a test compound in rats following single dose administration by infusion. Male Sprague-Dawley rats (n=3 per dose groups) are dosed with 50 mg/kg of a test compound. Two formulations are used: 30% PEG 400 and 10% sulfobutylether-β-cyclodextrin. Urine samples are cage collected over 24 hours. Blood samples are collected for serum chemistry and concentration determination. Liver and kidneys are removed for histology evaluation. One kidney and part of the liver are homogenized for concentration analysis using reverse phase HPLC with UV detection. Drug concentrations in urine and serum samples are determined by LC-MS analysis.

C. Tissue Distribution Following Multiple Doses

This procedure is used too evaluate the potential tissue accumulation of a test compound in rats following multiple dose administration by intravenous infusion. Male and female Sprague-Dawley rats (n=4 per sex per dose group) are dosed with a test compound at 12.5, 25 and 50 mg/kg per day for seven days. Animals are sacrificed at day 1 (n=3 per sex per dose group) following the last dose administered. One animal per sex per dose group is retained as recovery animal and sacrificed at day 7 following the last dose administered. The test compound is formulated in 5% hydroxypropyl-β-cyclodextrin or 1% sucrose/4.5% dextrose. Urine samples are cage collected at days 1 and 7 post-dose. Blood samples are collected for serum chemistry and concentration determination. Liver and kidneys are removed for histology evaluation. One kidney and part of the liver are homogenized for concentration analysis using reverse phase HPLC with UV detection. Drug concentrations in urine and serum samples are determined by LC-MS analysis.

Nephrotoxicity, histamine release and vascular irritation can be measured using procedures well-known to those skilled in the art.

Example 6

Determination of Tissue Accumulation and Nephrotoxicity

Female Sprague-Dawley rates (three per group) were dosed with Compound A (50 mg/kg) formulated in either hydroxypropyl-β-cyclodextrin or 5% dextrose/water or vehicle. The indicated doses were administered in a volume of 10 mL/kg via a 2-minute intravenous infusion. At 24 hours, the animals were sacrificed and serum and tissue samples collected. The results are shown in Tables 1 and 2.

TABLE 1

Tissue Distribution and Urinary Recovery for Compound A in Various Formulations Following Intravenous Infusion to Female Rats at a dose of 50 mg/kg.
(Values are Mean (SD))

| Compound (Formulation) | Serum Conc. (µg/mL) | % Recovered (as unchanged parent) | | |
|---|---|---|---|---|
| | | Urine | Liver | Kidney |
| Compound A (25% CD) | 0.86 (0.19) | 90.91 (8.39) | 1.90 (0.32) | 0.62 (0.12) |
| Compound A (5% CD) | 1.66 (0.33) | 40.51 (18.57) | 4.89 (0.81) | 2.08 (0.43) |
| Compound A (1% CD) | 17.1 (12.1) | 17.45 (6.92) | 8.47 (0.46) | 5.68 (2.49) |
| Compound A (D5W) | 59.8 (27.1) | 12.61 (4.60) | 14.19 (3.41) | 17.82 (4.94) |

CD = hydroxypropyl-β-cyclodextrin
D5W = aqueous 5% dextrose solution

As shown in Table 1, urinary recovery of Compound A was significantly higher in formulations contain a cyclodextrin; and liver and kidney accumulation were significantly lower in such formulations.

TABLE 2

Effects of Compound A Formulation on Serum Renal Chemistry

| Compound | Formulation | BUN (mg/dL) | Creatinine (mg/dL) |
|---|---|---|---|
| Vehicle | 25% (w/v) CD | 14 ± 1 | 0.26 ± 0.06 |
| Compound A | 25% (w/v) CD | 13 ± 2 | 0.26 ± 0.02 |
| Vehicle | 5% (w/v) CD | 10 ± 1 | 0.21 ± 0.01 |
| Compound A | 5% (w/v) CD | 18 ± 5 | 0.31 ± 0.07 |
| Vehicle | 1% (w/v) CD | 13 ± 2 | 0.24 ± 0.01 |
| Compound A | 1% (w/v) CD | 26 ± 5 | 0.34 ± 0.08 |
| Vehicle | D5W | 12 ± 2 | 0.28 ± 0.02 |
| Compound A | D5W | 67 ± 2 | 0.72 ± 0.08 |

CD = hydroxypropyl-β-cyclodextrin
D5W = aqueous 5% dextrose solution

The results in Table 2 show that the formulations containing cyclodextrin had significantly less nephrotoxicity compared to formulations without cyclodextrin.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. Additionally, all publications, patents, and patent documents cited hereinabove are incorporated by reference herein in full, as though individually incorporated by reference.

What is claimed is:

1. A method for reducing nephrotoxicity produced by a lipidated glycopeptide antibiotic in a mammal, the method comprising administering a therapeutically effective amount of the lipidated glycopeptide antibiotic or a pharmaceutically acceptable salt thereof to the mammal in a pharmaceutical composition comprising a cyclodextrin, wherein the lipidated glycopeptide antibiotic produces nephrotoxicity in the mammal in the absence of the cyclodextrin.

2. The method of claim 1, wherein the pharmaceutical composition further comprises water.

3. A method for reducing nephrotoxicity produced by a lipidated glycopeptide antibiotic in a mammal, the method comprising administering a therapeutically effective amount of the lipidated glycopeptide antibiotic or a pharmaceutically acceptable salt thereof to the mammal in a pharmaceutical composition comprising:
 (a) an aqueous cyclodextrin carrier, wherein the lipidated glycopeptide antibiotic produces nephrotoxicity in the mammal in the absence of the cyclodextrin.

4. A method for reducing nephrotoxicity produced by a lipidated glycopeptide antibiotic in a mammal, the method comprising administering a therapeutically effective amount of the lipidated glycopeptide antibiotic or a pharmaceutically acceptable salt thereof to the mammal in a pharmaceutical composition comprising:
 (a) 1 to 40 weight percent of a cyclodextrin; and
 60 to 99 weight percent of water, based on 100 weight percent of the composition, wherein the lipidated glycopeptide antibiotic produces nephrotoxicity in the mammal in the absence of the cyclodextrin.

5. The method of claim 4, wherein the cyclodextrin comprises about 5 to 35 weight percent of the composition.

6. The method of claim 4, wherein the cyclodextrin comprises about 10 to 30 weight percent of the composition.

7. The method of any one of claims 1 to 6, wherein the cyclodextrin is hydroxypropyl-β-cyclodextrin.

8. The method of any one of claims 1 to 6, wherein the cyclodextrin is sulfobutyl ether β-cyclodextrin.

* * * * *